United States Patent [19]

Marx et al.

[11] E Re. 30,287

[45] Reissued May 27, 1980

[54] 19 HYDROXY PROSTAGLANDINS

[75] Inventors: Arthur F. Marx, Delft; Jean Doodewaard, Schipluiden, both of Netherlands

[73] Assignee: Gist-Brocades N.V., Netherlands

[21] Appl. No.: 955,005

[22] Filed: Oct. 26, 1978

Related U.S. Patent Documents

Reissue of:

[64] Patent No.: 4,054,595
Issued: Oct. 18, 1977
Appl. No.: 561,895
Filed: Mar. 25, 1975

[30] Foreign Application Priority Data

Mar. 26, 1974 [GB] United Kingdom ..... 13399/74
Mar. 26, 1974 [GB] United Kingdom ..... 13400/74

[51] Int. Cl.[2] ..... C07C 177/00
[52] U.S. Cl. ..... 562/503; 260/438.1; 260/501.17; 424/305; 424/317; 560/121; 435/63; 435/886
[58] Field of Search ..... 560/121; 562/503

[56] References Cited

U.S. PATENT DOCUMENTS 3,878,046 4/1975 Marscheck ..... 560/121
3,903,143 9/1975 Muellen ..... 562/503

FOREIGN PATENT DOCUMENTS 2505519 8/1975 Fed. Rep. of Germany ..... 560/121
7207970 6/1972 Netherlands ..... 560/121

OTHER PUBLICATIONS

Taylor et al., Nature 250, 665 (1974).
Jonsson et al., Science, 187, 1093 (1975).

*Primary Examiner*—Robert Gerstl
*Attorney, Agent, or Firm*—Robert E. Burns; Emmanuel J. Lobato; Bruce L. Adams

[57] ABSTRACT

Novel 18ξ-, 19ξ- and 20ξ-hydroxy-prostaglandin derivatives of the formula I (I)

wherein the dotted line in the position 8–12 indicates the optional presence of a double bond, the waved lines in position 15 indicate that the hydroxyl group and the group $R_4$ are either in α- or β-position and Z represents a $—CH_2CH_2—$ or a cis —CH=CH— group, and wherein R represents one of the groups:

(wherein the waved lines indicate that the hydroxyl groups are either in α- or β-position and $R_1$ represents a hydrogen atom, a methyl or ethyl group), $R_2$ represents either an oxygen atom or a hydrogen atom and an α- or β-hydroxyl group, $R_3$ represents a hydrogen atom or a hydroxyl group and $R_4$ represents a hydrogen atom or a methyl group, with the proviso that when simultaneously, $R_1$, $R_3$ and $R_4$ each represents a hydrogen atom, $R_2$ represents an oxygen atom, a double bond is in 8–12 position and the 15-hydroxyl group is in position α, R does not represent the group (b), but that when in addition to these conditions, Z represents a cis —CH=CH— group and the 8–12 position is saturated, R either represents the groups (b) or (c); and the pharmaceutically acceptable salts and esters thereof, novel process for their preparation by selective microbiological hydroxylation of compounds of formula II

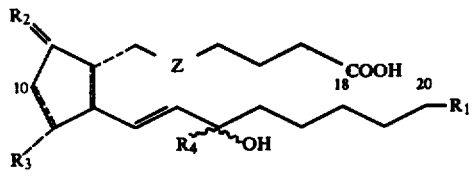

(II)

wherein the dotted line in the position 10–11 indicates the optional presence of a double bond in case the 8–12 position is saturated and the other symbols are as defined hereinabove, by means of microorganisms of the Division of Eumycota or, as far as the introduction of a hydroxyl group in the 18- or 19-position is concerned, of the Family of Streptomycetaceae, and, if desired, conversion of the 18- 19- and 20-hydroxy-prostaglandin derivatives thus obtained into pharmaceutically acceptable salts and esters thereof, and pharmaceutical compositions containing at least one of the novel hydroxy-prostaglandin derivatives of formula I.

2 Claims, 4 Drawing Figures

Figure 1:
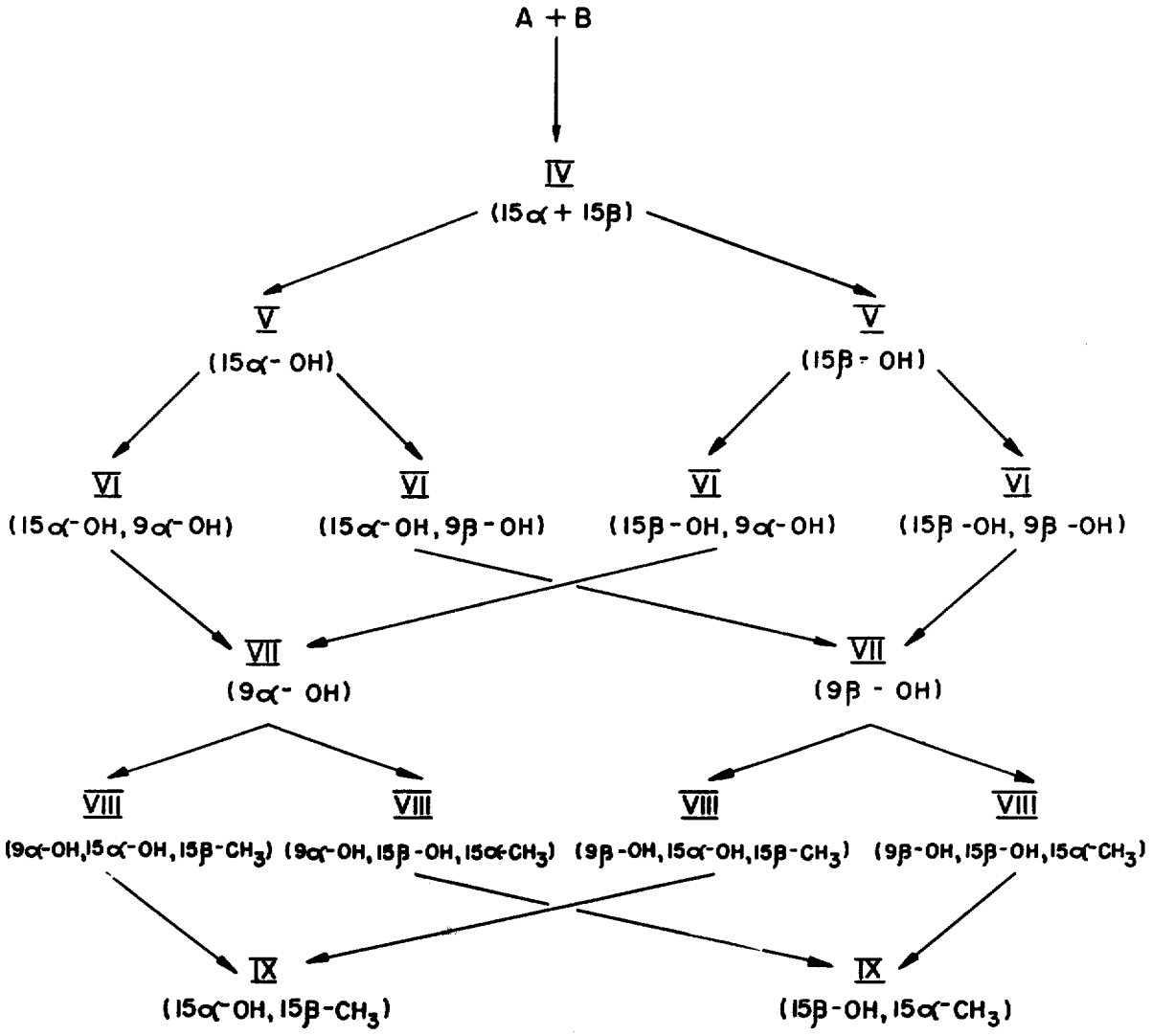

VI
(15β-OH, 9α-OH)

VI
(15β-OH, 9β-OH)

VII
(9α-OH)

VII
(9β-OH)

VIII
(9α-OH, 15α-OH, 15β-CH3)

VIII
(9β-OH, 15β-OH, 15α-CH3)

VIII
(9β-OH, 15α-OH, 15β-CH3)

VIII
(9β-OH, 15β-OH, 15α-CH3)

IX
(15α-OH, 15β-CH3)

IX
(15β-OH, 15α-CH3)

I

II

III

19 HYDROXY PROSTAGLANDINS

Matter enclosed in heavy brackets [ ] appears in the original patent but forms no part of this reissue specification; matter printed in italics indicates the additions made by reissue.

STATE OF THE ART

Prostaglandins are members of a new hormonal system with a remarkable range of biological and pharmaceutical properties. These compounds belong to a group of chemically related 20-carbon chain hydroxy fatty acids containing a five membered ring in the structure and different degress of unsaturation, a number of which have been reported in the literature. For a review on prostaglandins and the definition of primary prostaglandins, see for example, S. Bergström, Recent Progress in Hormone Research, 22, pp. 153–175 (1966) and Science, 157, p. 382 ff (1967) by the same author (Karim, editor; "Prostaglandins: Progress in Research" N.Y.-Wiley International (1972).

Prostaglandins are widely distributed in mammalian tissues and have been isolated from natural sources in very small amounts. In addition, a number of the naturally occurring prostaglandins have been prepared by chemical synthesis; note for example, J. Am. Chem. Soc., 91, p. 5675 ff (1969); J. Am. Chem. Soc., 92, p. 2586 ff (1970) and J. Am. Chem. Soc., 93, pages 1489–1493 (1971) and references cited therein; W. P. Schneider et al., J. Am. Chem. Soc., 90, p. 5895 ff (1968); U. Axen et al., Chem. Commun., p. 303 ff (1969) and W. P. Schneider, Chem. Commun., p. 304 ff (1969).

Because of the remarkable range of biological and pharmacological properties exhibited by this family of compounds, a great deal of interest has focused upon such compounds, and the preparation of analogs of such compounds.

Microbiological conversions of prostaglandins or of prostaglandin-type compounds have been described before, but these conversions usually relate to the reduction of keto groups, mostly by bacteria or yeasts, for example the conversion of 9,15-diketo-11-hydroxy-prosta-8(12),13(t)-dienoic acid by Flavobacterium and Pseudomonas species into 9-keto-11,15-dihydroxy-prosta-8(12),13(t)-dienoic acid (M. Miyano et al., Chem. Comm. (1971), 425).

U.S. Pat. No. 3,788,947 describes the fermentative reduction of the 10(11) double bond in PGA-type prostaglandins, sometimes accompanied by concomitant transformations, such as reduction of the 13(14) double bond or oxidation of the 15-hydroxyl group to a 15-oxo group. In one particular case, viz. reduction of the 10(11) double bond in 9-keto-15α-hydroxy-prosta-5(c),10,13(t)-trienoic acid ($PGA_2$) with Cunninghamella blakesleeana (ATCC 9245), there is described the concurrent introduction of a 18-hydroxyl group.

The 19-hydroxyl derivatives of $PGB_1$ (9-keto-15α-hydroxy-prosta-8(12),13(t)-dienoic acid) and $PGB_2$ (9-keto-15α-hydroxy-prosta-5(c),8(12),13(t)-trienoic acid) are described by S. Bergström, Science 157, p. 382 ff (1967).

OBJECTS OF THE INVENTION

It is an object of the invention to provide the novel hydroxy-prostaglandin derivatives of formula I shown below.

It is another object of the invention to provide a novel process for the preparation of the hydroxy-prostaglandins of said formula I by selective microbiological hydroxylation of compound of formula II shown below.

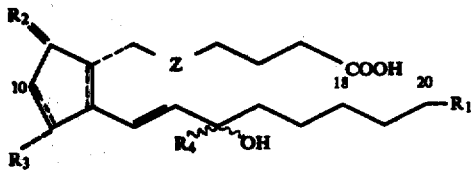

(II)

It is a further object of the invention to provide pharmaceutical compositions for the treatment of bronchial asthma and other bronchiospastic conditions, which comprise at least one of the hydroxy-prostaglandin derivatives of formula I, as well as a method for the treatment of bronchial asthma or other bronchiospastic conditions by administration of these pharmaceutical compositions.

THE INVENTION

The prostaglandin derivatives of the present invention are the new 18{-, 19{- and 20{-hydroxy-prostaglandin derivatives of the formula I

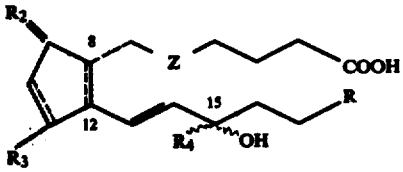

(I)

wherein the dotted line in the position 8–12 indicates the optional presence of a double bond, the waved lines in position 15 indicate that the hydroxyl group and the group $R_4$ are either in α- or β-position and Z represents a $—CH_2CH_2—$ or a cis —CH=CH— group, and wherein R represents one of the groups:

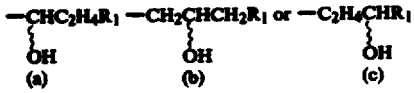

(wherein the waved lines indicate that the hydroxyl groups are either in α- or β-position and $R_1$ represents a hydrogen atom, a methyl or ethyl group), $R_2$ represents either an oxygen atom or a hydrogen atom and an α- or β-hydroxyl group, $R_3$ represents a hydrogen atom or a hydroxyl group and $R_4$ represents a hydrogen atom or a methyl group, with the proviso that when simultaneously, $R_1$, $R_3$ and $R_4$ each represents a hydrogen atom, $R_2$ represents an oxygen atom, a double bond is in 8–12 position and the 15-hydroxyl group is in position α, R does not represent the group (b), but that when in addition to these conditions, Z represents a cis —CH=CH— group and the 8–12 position is saturated, R either represents the groups (b) or (c); and the pharmaceutically acceptable salts and esters thereof.

The present invention provides also a process for the selective microbiological introduction of a hydroxyl group in the 18-, 19- or 20-position of prostaglandins and prostaglandin-type compounds, which comprises subjecting a compound of the general formula II, wherein the dotted line in the position 10–11 indicates the optional presence of a double bond in case the 8–12 position is saturated and the other symbols are as defined hereinabove, to the hydroxylation activity of microorganism (or enzymes thereof) of the Division of Eumycota (Kingdom of Fungi) or, as far as the introduction of a hydroxyl group in the 18- or 19-position is concerned, of the Family of Streptomycetaceae (Order Actinomycetales, Class Schizomycetes, Division Protophyta of the Kingdom of Plants).

The 18ξ-, 19ξ- and 20ξ-hydroxy-prostaglandin derivatives thus obtained can be converted into pharmaceutically acceptable salts and esters thereof, by reacting the corresponding compound in the form of a free acid with a suitable organic or inorganic base or ester-forming derivative.

Microbiological conversions of prostaglandins or of prostaglandin-type compounds have been described before, but these conversions usually relate to the reduction of keto groups, mostly by bacteria or yeasts, for example the conversion of 9,15-diketo-11-hydroxy-prosta-8(12),13(t)-dienoic acid by Flavobacterium and Pseudomonas species into 9-keto-11,15-dihydroxy-prosta-8(12),13(t)-dienoic acid (M. Miyano et al., Chem. Comm. (1971), 425).

U.S. Pat. No. 3,788,947 describes the fermentative reduction of the 10(11) double bond in PGA-type prostaglandins, sometimes accompanied by concomitant transformations, such as reduction of the 13(14) double bond or oxidation of the 15-hydroxy group to a 15-oxo group. In one particular case, viz. reduction of the 10(11) double bond in 9-keto-15α-hydroxy-prosta-5(c),10,13(t)-trienoic acid ($PGA_2$) with Cunninghamella blakesleeana (ATCC 9245), there is described the concurrent introduction of a 18-hydroxyl group.

The 19-hydroxyl derivatives of $PGB_1$ (9-keto-15α-hydroxy-prosta8(12),13(t)-dienoic acid) and $PGB_2$ (9-keto-15α-hydroxy-prosta-5(c),8(12),13(t)-trienoic acid) are described by S. Bergstrom, Science 157, p. 382 ff (1967).

Figure 2:
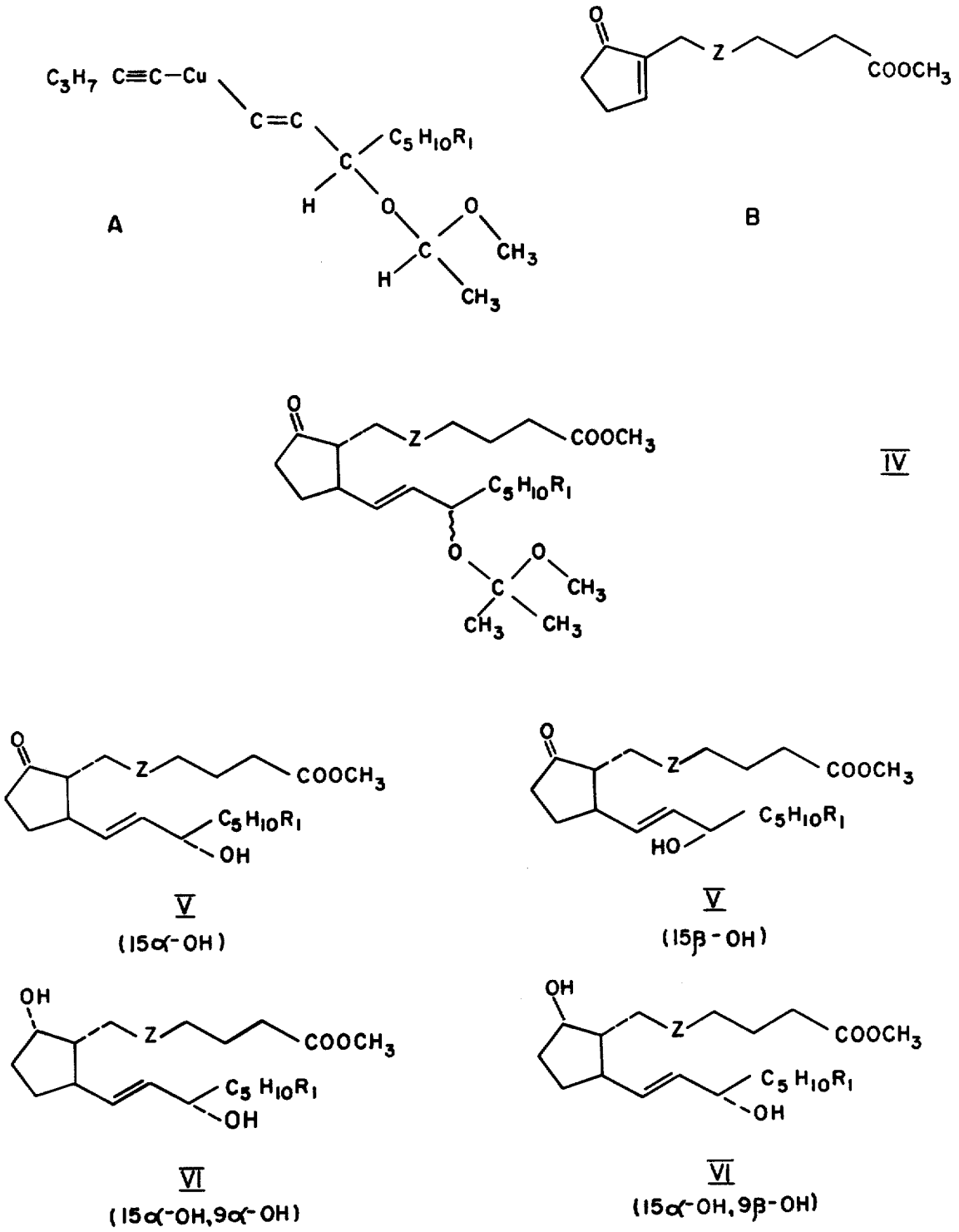
Figure 2:
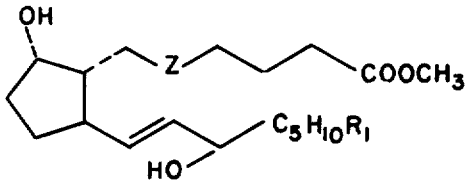
Figure 2:
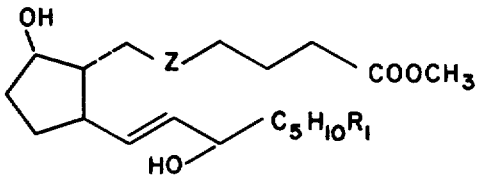
Figure 2:
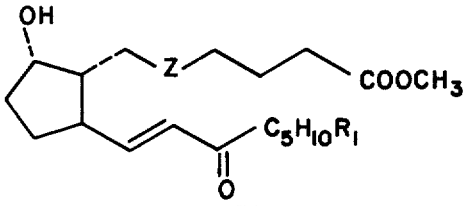
Figure 2:
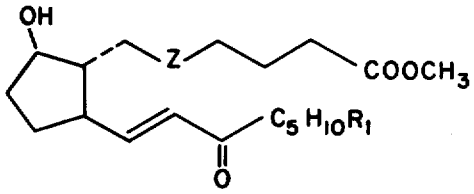
Figure 2:
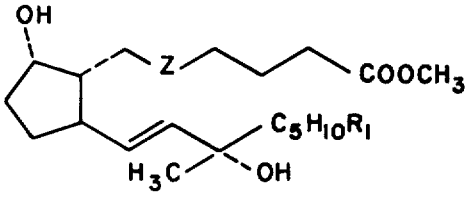
Figure 2:
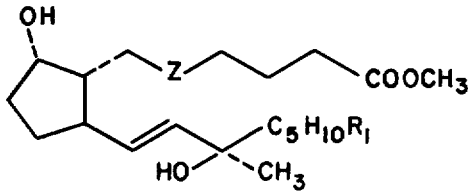
Figure 2:
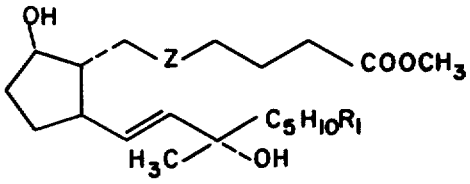
Figure 2:
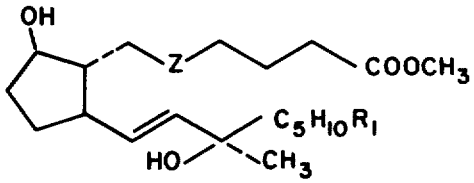
Figure 2:
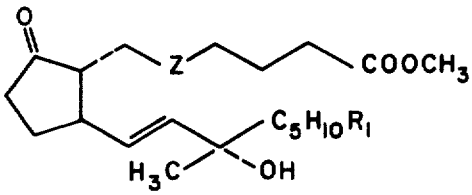
Figure 2:
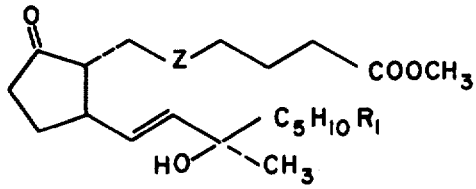
Figure 3:
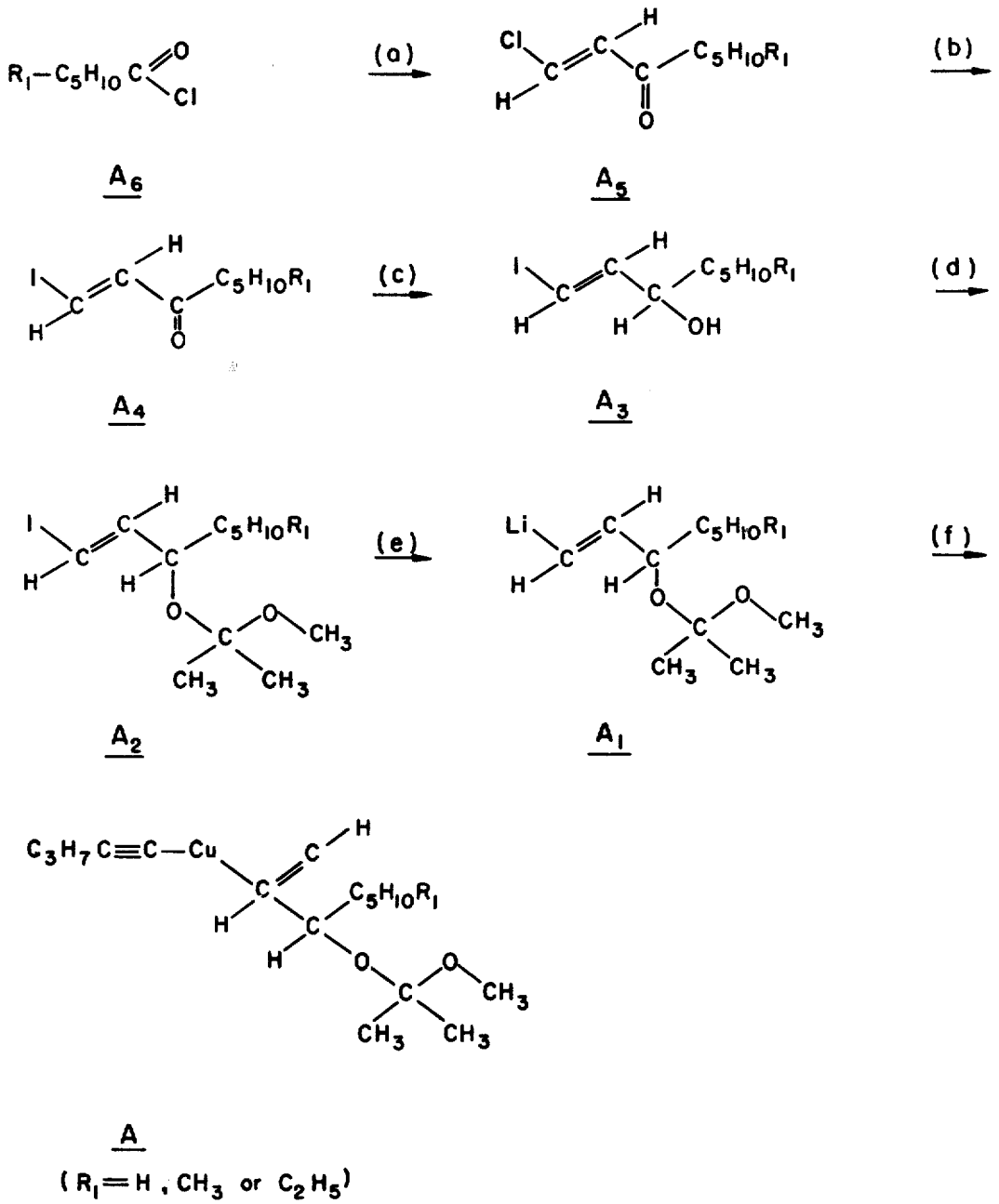
Figure 4:
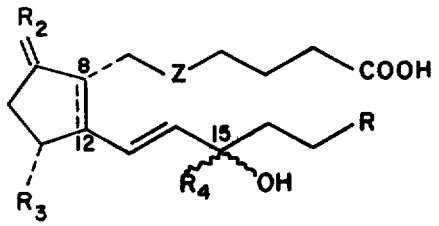
Figure 4:
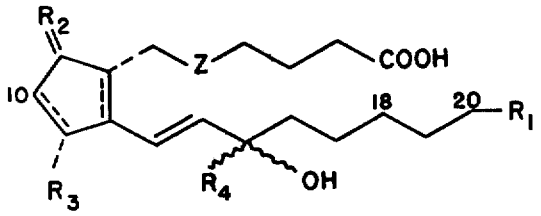
Figure 4:
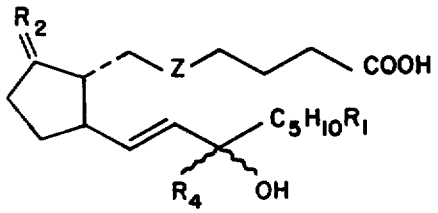

The invention will be described with reference to the accompanying drawings wherein FIG. 1 shows the reaction synthesis scheme for the preparation of the starting materials for this invention from known starting materials;

FIG. 2 and FIG. 2 continued are the structural formula of the compounds obtained as intermediates in the synthesis scheme shown in FIG. 1;

FIG. 3 shows the structural formula of the intermediates formed in synthesis of Compound A used as a starting material for the synthesis scheme of FIG. 1. The preparation of these intermediates $A_6$ to $A_1$ and A is described in the Preparation section of the Specification and FIG. 4 shows the structural formula of compound of Formula I of the invention prepared as described from the compounds of Formula II and III also shown.

The 18ξ-, 19ξ- and 20ξ-hydroxy-prostaglandin derivatives of formula I supra are potent agents in the treatment of bronchial asthma and other bronchospastic conditions. They have considerable relaxant activity on respiratory smooth muscle, whereas they were found, in general, to be devoid of appreciable activity on the intestinal and uterine smooth muscle, as well as of appreciable irritant activity at the site of application.

The utility of various prostaglandins and prostaglandin-derivatives presently in use in clinic is limited due to the occurrence of undesirable side-effects, such as diarrhoea, abdominal cramps and/or irritation at the site of application.

The selective activity of the hydroxy-prostaglandin derivatives of the present invention was established by a multiparameter guinea-pig test. In this test guinea-pigs weighing 600–900 g are anaesthetized with sodium pentobarbitone (45 mg/kg, i.p.). Supplementary doses of sodium pentobarbitone (3–6 mg i.v.) are administered when required (i.e. when spontaneous respiration appears). The jugular vein is cannulated for the administration of drugs. The guinea-pig is artificially respired with $N_2O/O_2$ (7/3), using a Keuskamp respirator.

Then the following functions are measured:

a. Blood pressure.

The common carotid artery is cannulated and the blood pressure measured with a pressure transducer.

b. Bronchial resistance and tracheal segment pressure.

A cannula is inserted into the trachea as close as possible to the thorax. The guinea-pig is artificially ventilated at 55 strokes/min. The pressure changes, assumed to be due to changes caused by the bronchioles, are measured by a pressure transducer attached to a side arm of the cannula. The trachea is occluded at its lower end with a blind-ended cannula, while a cannula is further introduced into the trachea as close as possible to the larynx. The system is completely filled with saline, and connected to a very sensitive pressure transducer. Changes in the pressure measured (cm $H_2O$) are assumed to reflect changes in the tone of the smooth muscle of the trachea. The trachea segment cannula is inserted with extreme caution so as to avoid disruption of the nerve or blood supply to the segment.

c. Measurement of intestinal motility.

A balloon, containing distilled water and connected to a pressure transducer, is inserted in the duodenum of the guinea-pig. Care is taken on ligaturing the cannula to avoid stricture of the duodenum. The balloon is at a pressure of 10–20 mm Hg.

d. Measurement of uterine motility.

A polyethylene cannula is inserted into the uterus via the vagina to a depth of 2.5 cm. This is then tied off with a ligature around the cervix. The cannula is connected to a pressure transducer, the whole system being filled with liquid paraffin at a pressure of 10–20 mm Hg.

The present hydroxy-prostaglandin derivatives compare favourably in this multiparameter test with well-known prostaglandins, such as $PGF_{2\alpha}$ and $PGE_1$, as is demonstrated for some compounds of this invention by Table 1.

TABLE 1

| | Guinea-pig Multiparameter test. | | | | |
|---|---|---|---|---|---|
| COMPOUND | DOSE in μg | TRACHEAL segment pressure | BRONCHIAL resistance | INTESTINAL contractions | UTERINE contractions |
| $PGF_{2\alpha}$ | 20 | + | + | + | ++ |
| $PGE_1$ | 5 | – | 0 | + | 0 |

TABLE 1-continued

| COMPOUND | DOSE in μg | Guinea-pig Multiparameter test. TRACHEAL segment pressure | BRONCHIAL resistance | INTESTINAL contractions | UTERINE contractions |
|---|---|---|---|---|---|
| 9-keto-15α,18ξ-dihydroxy-prost-13(t)-enoic acid | 100 | – | 0 | 0 | 0 |
| 9-keto-15α,19ξ-dihydroxy-prost-13(t)-enoic acid | 100 | – | 0 | 0 | 0 |
| 9β,15α,18 -trihydroxy-prost-13(t)-enoic acid | 500 | –0 | 0 | 0 | |
| 9β,15α,19 -trihydroxy-prost-13(t)-enoic acid | 500 | – | 0 | 0 | 0 |
| 9β,15α,20-trihydroxy-prost-13(t)-enoic acid | 500 | – | 0 | 0 | 0 |

The activity of the 18ξ-, 19ξ- and 20ξ-hydroxy-prostaglandin derivatives on the respiratory tract musculature was further confirmed by determination of their ability to antagonize histamine-induced bronchoconstriction. This test is a modification of the guinea-pig multiparameter test, cannulations being carried out only for recording blood pressure, tracheal segment pressure and bronchial resistance.

Histamine was injected i.v. in a dose of 4 μg (as base) at regular intervals throughout the experiment. If extra dosed of sodium pentobarbitone had to be administered during the course of the experiment to suppress voluntary respiration, the interval to the next dose of histamine was lengthened.

Test compound were injected i.v. one minute before histamine in volumes less than 0.5 ml. The substances were washed in with 0.3 ml sterile saline. The lungs were artificially over-ventilated one minute prior to injection of the test compounds.

The ability of the compounds to counteract histamine-induced bronchoconstriction and the increase in tracheal segment pressure was determined using two dose level—a low one and a high one.

Some of the results obtained with compounds according to this invention, using $PGE_1$ as the reference compound, are shown in Table 2.

TABLE 2

| COMPOUND | DOSE in μg | Antagonism of Histamine-induced Broncho-constriction (guinea-pig) % INHIBITION (± S.D.) |
|---|---|---|
| $PGE_1$ | 0.1 | 27.6 (± 10.5) |
| | 1.0 | 53.2 (± 14.8) |
| | 5.0 | about 88 |
| 9-keto-15α,18ξ-dihydroxy-prost-13(t)-enoic acid | 1.0 | 25.9 (± 6) |
| | 100 | about 80 |
| 9-keto-15α,19ξ-dihydroxy-prost-13(t)-enoic acid | 1 | 23.9 (± 13.4) |
| | 100 | 88.1 (± 5.0) |
| 9β,15α,18ξ-trihydroxy-prost-13(t)-enoic acid | 100 | 28.1 (± 15.2) |
| 19β,15α,19ξ-trihydroxy-prost-13(t)-enoic acid | 100 | 62.5 (± 6.6) |
| 19β,15α,20-trihydroxy-prost-13(t)-enoic acid | 100 | 52.9 (± 17.9) |
| 9α,15β,19ξ-trihydroxy-prost-13(t)-enoic acid | 500 | about 60 |
| 9-keto-15β,19ξ-dihydroxy-prost-13(t)-enoic acid | 500 | about 85 |
| 9-keto-15α,18ξ-dihydroxy-prost-5(c),13(t)-dienoic acid | 1 | 45 (± 8.8) |
| 9-keto-15α,19ξ-dihydroxy-prosta-5(c),13(t)-dienoic acid | 1 | 50.3 (± 4.3) |
| 9-keto-15α,20-dihydroxy-prosta 5(c),13(t)-dienoic acid | 1 | 60.7 (± 14.6) |
| 9-keto-11α,15α,18 trihydroxy-prost-13(t)-enoic acid | 1 | about 70 |
| 9-keto-11α,15α,19ξ-trihydroxy-prost-13(t)-enoic acid | 1 | about 60 |
| 9-keto-11α,15α,18ξ-trihydroxy-prosta-5(c),13(t)-dienoic acid | 1 | about 35 |
| 9-keto-11α,15α,19ξ-trihydroxy-prosta-5(c),13(t)-dienoic acid | 1 | about 70 |

The irritation at the site of application which is shown by various prostaglandins and prostaglandin-derivatives can result in phlebitis at the site of injection or in persistant coughing if (as in the case f.e. with $PGE_1$ and $PGE_2$) an aerosol is employed.

This effect can be studied using the Draize scoring method for determining irritation following topical application in the rabbit eye. $PGE_1$ was used as the reference compound; 1 μg/eye was the threshold irritant dose with this compound; 5 μg was definitely irritant. Doses of the present hydroxy-prostaglandin derivatives which were equi-effective or moe effective than $PGE_1$ against histamine-induced bronchoconstriction, proved not to irritate the rabbit eye by topical application. The results for some compounds of the invention are given in Table 3.

TABLE 3

| COMPOUND | DOSE in μg | IRRITATION |
|---|---|---|
| $PGE_1$ | 5 | + |
| 9-keto-15α,19ξ-dihydroxy-prost-13(t)-enoic acid | 100 | – |
| 9-keto-15α,20-dihydroxy-prosta-5(c),13(t)-dienoic acid | 100 | – |
| 9-keto-11α,15α,19ξ-trihydroxy-prost-13(t)-enoic acid | 25 | – |
| 9-keto-11α,15α,19ξ-trihydroxy-prosta-5(c),13(t)-dienoic acid | 25 | – |

From the results obtained it may be concluded in view of the explanations give above, that the 18 -, 19 - and 20 -prostaglandin derivatives of the present invention are particularly useful for the treatment of bronchial asthma and other bronchospastic conditions. Their advantages over various of the presently available prostaglandin derivatives, are that they either have greater specificity (i.e. less or absent activity on the intestines) or are less irritant at the site of application, or both.

Specific new prostaglandin compounds of this invention are the 18ξ-, and 19ξ- and 20ξ-hydroxy derivatives of the following prostaglandins and prostaglandin-type compounds:

9-keto-15α-hydroxy-prosta-5(c),13(t)-dienoic acid;
9-keto-15α-hydroxy-prosta-5(c)8(12),13(t)-trienoic acid;
9-keto-11α,15α-dihydroxy-prost-13(t)-enoic acid;
9-keto-11α,15α-dihydroxy-prosta-5(c)-13(t)-dienoic acid;
9α,11α,15α-trihydroxy-prosta-5(c),13(t)-dienoic acid;
9-keto-15α-hydroxy-prost-13(t)-enoic acid;
9α,15α-dihydroxy-prost-13(t)-enoic acid;
9β,15α-dihydroxy-prost-13(t)-enoic acid;
9-keto-15β-hydroxy-prost-13(t)-enoic acid;
9-keto-15β-hydroxy-prost-13(t)-enoic acid;
9β,15β-dihydroxy-prost-13(t)-enoic acid;
9α,15α-dihydroxy-15β-methyl-prost-13(t)-enoic acid;
9α,15α-dihydroxy-20-ethyl-prost-13(t)-enoic acid;
9-keto-15α-hydroxy-15βmethyl 20-ethyl-prost-13(t)-enoic acid;
9-keto-15β-hydroxy-15α-methyl-20-ethyl-prost-13(t)-enoic acid;
9α,15α-dihydroxy-15β-methyl-20-ethyl-prost-13(t)-enoic acid;
9α,15β-dihydroxy-15α-methyl-20-ethyl-prost-13(t)-enoic acid.

Specific prostaglandins and prostaglandin-type compounds of the general formula II supra which can be microbiologically hydroxylated according to the process of this invention include:

9-keto-15α-hydroxy-prosta-5(c)-10,13(t)-trienoic acid;
9-keto-15α-hydroxy-prosta-5(c)8(12),13(t)-trienoic acid;
9-keto-11α,15α-dihydroxy-prost-13(t)-enoic acid;
9-keto-11α,15α-dihydroxy-prosta-5(c)13(t)-dienoic acid;
9α,11α,15α-trihydroxy-prost-13(t)-enoic acid;
9β,11α,15α-trihydroxy-prost-13(t)-enoic acid;
9α,11α,15α-trihydroxy-prosta-5(c),13(t)-dienoic acid;
9β,11α,15α-trihydroxy-prosta-5(c),13(t)-dienoic acid;
dl-9α,15α-dihydroxy-prost-13(t)-enoic acid;
dl-9β,15α-dihydroxy-prost-13(t)-enoic acid;
dl-9α,15β-dihydroxy-prost-13(t)-enoic acid;
dl-9β,15β-dihydroxy-prost-13(t)-enoic acid;
dl-9-keto-15α-hydroxy-prost-13(t)-enoic acid;
dl-9-keto-15β-hydroxy-prost-13(t)-enoic acid;
dl-9α,15α-dihydroxy-prosta-5(c),13(t)-denoic acid;
dl-9β,15α-dihydroxy-prosta-5(c),13(t)-dienoic acid;
dl-9α,15β-dihydroxy-prosta-5(c),13(t)-dienoic acid;
dl-9β,15β-dihydroxy-prosta-5(c),13(t)-dienoic acid;
dl-9-keto-15α-hydroxy-prosta-5(c),13(t)-dienoic acid;
dl-9-keto-15β-hydroxy-prosta-5(c),13(t)-dienoic acid;
dl-9α,15α-dihydroxy-15β-methyl-prost-13(t)-enoic acid;
dl-9α,15β-dihydroxy-15α-methyl-prost-13(t)-enoic acid;
dl-9β,15α-dihydroxy-15β-methyl-prost-13(t)-enoic acid;
dl-9β,15β-dihydroxy-15α-methyl-prost-13(t)-enoic acid;
dl-9-keto-15α-hydroxy-15β-methyl-prost-13(t)-enoic acid;
dl-9-keto-15β-hydroxy-15α-methyl-prost-13(t)-enoic acid;
dl-9α,15α-dihydroxy-15β-methyl-prosta-5(c),13(t)-dienoic acid;
dl-9α,15β-dihydroxy-15α-methyl-prosta-5(c),13(t)-dienoic acid;
dl-9β,15α-dihydroxy-15βmethyl-prosta-5(c),13(t)-dienoic acid;
dl-9β,15β-dihydroxy-15αmethyl-prosta-5(c),13(t)-dienoic acid;
dl-9-keto-15α-hydroxy-15β-methyl-prosta-5(c),13(t)-dienoic acid;
dl-9-keto-15β-hydroxy-15α-methyl-prosta-5(c),13(t)-dienoic acid;
dl-9α,15α-dihydroxy-20-methyl-prost-13(t)-enoic acid;
dl-9β,15α-dihydroxy-20-methyl-prost-13(t)-enoic acid;
dl-9α,15β-dihydroxy-20-methyl-prost-13(t)-enoic acid;
dl-9β,15β-dihydroxy-20-methyl-prost-13(t)-enoic acid;
dl-9-keto-15α-hydroxy-20-methyl-prost-13(t)-enoic acid;
dl-9-keto-15β-hydroxy-20-methyl-prost-13(t)-enoic acid;
dl-9α,15α-dihydroxy-20-methyl-prosta-5(c),13(t)-dienoic acid;
dl-9β,15α-dihydroxy-20-methyl-prosta-5(c),13(t)-dienoic acid;
dl-9α,15β-dihydroxy-20-methyl-prosta-5(c),13(t)-dienoic acid;
dl-9β,15β-dihydroxy-20-methyl-prosta-5(c),13(t)-dienoic acid;
dl-9-keto-15α-hydroxy-20-methyl-prosta-5(c),13(t)-dienoic acid;
dl-9-keto-15β-hydroxy-20-methyl-prosta-5(c),13(t)-dienoic acid;
dl-9α,15α-dihydroxy-20-ethyl-prost-13(t)-enoic acid;
dl-9β,15α-dihydroxy-20-ethyl-prost-13(t)-enoic acid;
dl-9α,15β-dihydroxy-20-ethyl-prost-13(t)-enoic acid;
dl-9β,15β-dihydroxy-20-ethyl-prost-13(t)-enoic acid;
dl-9-keto-15α-hydroxy-20-ethyl-prost-13(t)-enoic acid;
dl-9-keto-15β-hydroxy-20-ethyl-prost-13(t)-enoic acid;
dl-9α,15α-dihydroxy-20-ethyl-prosta-5(c),13(t)-dienoic acid;
dl-9β,15α-dihydroxy-20-ethyl-prosta-5(c),13(t)-dienoic acid;
dl-9α,15β-dihydroxy-20-ethyl-prosta-5(c),13(t)-dienoic acid;
dl-9β,15β-dihydroxy-20-ethyl-prosta-5(c),13(t)-dienoic acid;
dl-9-keto-15α-hydroxy-20-ethyl-prosta-5(c),13(t)-dienoic acid;
dl-9-keto-15β-hydroxy-20-ethyl-prosta-5(c),13(t)-dienoic acid;
dl-9α,15α- dihydroxy-15β-methyl-20-methyl-prost-13(t)-enoic acid;
dl-9α,15β-dihydroxy-15α-methyl-20-methyl-prost-13(t)-enoic acid;
dl-9β,15α-dihydroxy-15β-methyl-20-methyl-prost-13(t)-enoic acid;
dl-9β,15β-dihydroxy-15α-methyl-20-methyl-prost-13(t)-enoic acid;
dl-9-keto-15α-hydroxy-15β-methyl-20-methyl-prost-13(t)-enoic acid;
dl-9-keto-15β-hydroxy-15α-methyl-20-methyl-prost-13(t)-enoic acid;
dl-9α,15α-dihydroxy-15β-methyl-20-methyl-prosta-5(c),13(t)-dienoic acid;
dl-9α,15β-dihydroxy-15α-methyl-20-methyl-prosta-5(c),13(t)-dienoic acid;
dl-9β,15α-dihydroxy-15β-methyl-20-methyl-prosta-5(c),13(t)-dienoic acid;

dl-9β,15β-dihydroxy-15α-methyl-20-methyl-prosta-5(c),13(t)-dienoic acid;

dl-9-keto-15α-hydroxy-15β-methyl-20-methyl-prosta-5(c),13(t)-dienoic acid;

dl-9-keto-15β-hydroxy-15α-methyl-20-methyl-prosta-5(c),13(t)-dienoic acid;

dl-9α,15α-dihydroxy-15β-methyl-20-ethyl-prost-13(t)-enoic acid;

dl-9α,15β-dihydroxy-15α-methyl-20-ethyl-prost-13(t)-enoic acid;

dl-9β,15α-dihydroxy-15β-methyl-20-ethyl-prost-13(t)-enoic acid;

dl-9β,15β-dihydroxy-15α-methyl-20-ethyl-prost-13(t)-enoic acid;

dl-9-keto-15α-hydroxy-15β-methyl-20-ethyl-prost-13(t)-enoic acid;

dl-9-keto-15β-hydroxy-15α-methyl-20-ethyl-prost-13(t)-enoic acid;

dl-9α,15α-dihydroxy-15β-methyl-20-ethyl-prosta-5(c),13(t)-dienoic acid;

dl-9α,15β-dihydroxy-15α-methyl-20-ethyl-prosta-5(c),13(t)-dienoic acid;

dl-9β,15α-dihydroxy-15β-methyl-20-ethyl-prosta-5(c),13(t)-dienoic acid;

dl-9β,15β-dihydroxy-15α-methyl-20-ethyl-prosta-5(c),13(t)-dienoic acid;

dl-9-keto-15α-hydroxy-15β-methyl-20-ethyl-prosta-5(c),13(t)-dienoic acid;

dl-9-keto-15β-hydroxy-15α-methyl-20-ethyl-prosta-5(c),13(t)-dienoic acid;

Some of the starting materials useful in preparing the novel 18ξ-, 19ξ- and 20ξ-hydroxy-prostagandin derivatives of general formula I supra are known substances, such as:

9-keto-15α-hydroxy-prosta-5(c),10,13(t)-trienoic acid ($PGA_2$);

9-keto-15α-hydroxy-prosta-5(c),8(12),13(t)-trienoic acid ($PGB_2$);

9-keto-11α,15α-dihydroxy-prost-13(t)-enoic acid ($PGE_1$);

9-keto-11α,15α-dihydroxy-prosta-5(c),13(t)-dienoic acid ($PGE_2$);

9α,11α,15α-trihydroxy-prost-13(t)-enoic acid ($PGF_{1\alpha}$);

9β,11α,15α-trihydroxy-prost-13(t)-enoic acid ($PGF_{1\beta}$);

9α,11α,15α-trihydroxy-prosta-5(c),13(t)-dienoic acid ($PGF_{2\alpha}$);

9β,11α,15α-trihydroxy-prosta-5(c),13(t)-dienoic acid $PGF_{2\beta}$).

Other starting materials in the process of this invention with the formula III

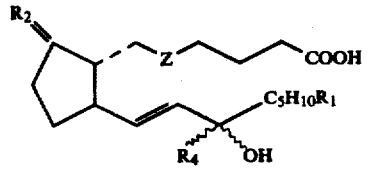

(III)

wherein Z, $R_1$, $R_2$ and $R_4$ are as hereinbefore defined, can be prepared according to the abbreviated schematic reaction sequence shown in FIG. 1, wherein each of the symbols A, B, IV and V through IX represents compounds which may be depicted structurally by the formulas shown in FIG. 2, wherein Z and $R_1$ are as hereinbefore defined and the waved line in formula IV indicates a mixture of the α- and β-isomer.

The compounds of formula III (the free acids) are obtained by alkaline hydrolysis of the corresponding methyl esters of the formulas V, VI, VIII and IX shown in FIG. 2.

The compounds of formula A, wherein $R_1$ is as hereinbefore defined, which are starting material in the reaction sequence shown in FIG. 2, are conveniently prepared according to the schematic overall reaction sequence shown in FIG. 3.

The compounds of formula A are prepared as follows: Step (a) is effected by treating the compounds of formula $A_6$ with acetylene in the presence of aluminium chloride at 0° C. to yield the compounds of formula $A_5$. The reaction is usually complete within four hours.

Step (b) is effected by treating the compounds of formula $A_5$ with sodium iodide under anhydrous conditions and is typically conducted under reflux in acetone until the reaction is complete, usually from three to twelve hours, to obtain the compounds of formula $A_4$.

Step (c) is carried out by treating compounds of formula $A_4$ with [sodium bis(2-methoxy ethoxy)aluminium hydride] and subsequently with an acid, e.g., sulfuric acid, at 0° C. to obtain the compounds of formula $A_3$.

Step (d) is conveniently effected by treating the compounds of formula $A_3$ with isopropenyl methyl ether in the presence of an acid catalyst e.g., dichloroacetic acid or phosphorous oxychloride, at 0° C. The compound of formula $A_2$ wherein $R_1$ is a hydrogen atom, is also disclosed by Kluge et al., J. Am. Chem. Soc., 94, 7827 (1972).

Step (e) is effected by treating compounds of formula $A_2$ with t-butyl lithium at −78° C. to yield the compounds of formula $A_1$.

The last step of the above preparation, step (f), is conveniently effected by adding a solution of the compounds of formula $A_1$ to a solution of copper pentyne and hexamethyl phosphorous triamide to obtain the compounds of formula A. The reaction is carried out at −78° C. and is usually complete within one hour.

The compounds of formula IV are conveniently prepared by adding to the freshly prepared compounds of formula A, the preparation of which is described above, a compound of formula B, described by Bagli et al. in Tetrahedron Letters, 465–470 (1966). The reaction is conveniently carried out at −78° C. and yields a mixture of two isomers of formula IV.

The compounds of formula V are conveniently prepared by removing the ether protecting group by treating the above obtained mixture of compounds of formula IV with acetic acid at room temperature. The resulting mixture of the compounds of formula V is separated into its isomers (15α-OH and 15β-OH) by means of chromatography on silica gel using ethyl acetate/hexane of increasing polarity as solvent.

The thus obtained compounds of formula V (15α-OH) are converted to a mixture of the isomers of the compounds of formula VI (15α-OH, 9α-OH and 15α-OH, 9β-OH) by treatment with sodium borohydride at 0° C. The reaction is complete within about 45 minutes. The mixture of isomers is then chromatographed on silica gel using ethyl acetate/hexane of increasing polarity as the solvent to obtain the compounds of formula VI (15α-OH, 9α-OH and 15α-OH, 9β-OH). Tn a similar manner the above-obtained compounds of formula V (15β-OH) are converted into the individual isomers, the compounds of formula VI (15β-OH, 9α-OH and 15β-

OH, 9β-OH). The thus obtained compounds of formula VI (15α-OH, 9α-OH or 15β-OH, 9α-OH) are treated with dichlorodicyano quinone for 36 hours at room temperature in a benzene solution to yield the compounds of formula VII (9α-OH). Similarly, substituting the compounds of formula VI (15α-OH, 9β-OH or 15β-OH, 9β-OH) for the compounds of formula VI (15α-OH, 9α-OH) yields the compounds of formula VII (9β-OH).

Treatment of the compounds of formula VII (9α-OH) with methylmagnesium bromide in tetrahydrofuran at −30° C. for 45 minutes yields a mixture of compounds of formula VIII (9α-OH, 15α-OH, 15β-$CH_3$ and 9α-OH, 15β-OH, 15α-$CH_3$), which are separated into individual isomers by chromatography on silica gel using ethyl acetate/hexane of increasing polarity as solvent. Substituting the compounds of formula VII (9β-OH) for VII (9α-OH) in the above reaction yields the compounds of formula VIII (9β-OH, 15α-OH, 15β-$CH_3$ and 9β-OH, 15β-OH, 15α-$CH_3$).

The thus obtained compounds of formula VIII (9α-OH, 15α-OH, 15β-$CH_3$) are treated with a suspension of Celite (diatomaceous earth) and chromium trioxide in anhydrous methylene chloride under nitrogen in the presence of pyridine for about one hour to yield the compounds of formula IX (15α-OH, 15β-$CH_3$). The latter compound is also obtained by substituting the compounds of formula VIII (9β-OH, 15α-OH, 15β-$CH_3$) for the compounds of formula VIII (9α-OH, 15α-OH, 15β-$CH_3$). Substituting the compounds of formula VIII (9α-OH, 15β-OH, 15α-$CH_3$ or 9β-OH, 15β-OH, 15α-$CH_3$) for the compounds of formula VIII (9α-OH, 15α-OH, 15β-$CH_3$) yields the compounds of formula IX (15β-OH, 15α-$CH_3$).

The compounds of formulas V, VI, VIII and IX are converted to their corresponding free acids by treatment with base, e.g., potassium hydroxide at room temperature for about 2 hours, to yield the compounds of formula III.

PREPARATION 1

This preparation illustrates methods for preparing dl-1-pentynyl-1-[trans-3-(2,2-methoxypropoxy)-1decenyl]cuprate. (A, $R_1=C_2H_5$)

a. A solution of 200 ml of octanoyl chloride ($A_6$, $R_1=C_2H_5$) in 750 ml of carbon tetrachloride is cooled on an ice bath and treated with 214 g of aluminium chloride in three portions over a 1 hour period while acetylene is bubbled through the solution. The ice bath is removed and the reaction mixture stirred at room temperature for 3 hours with additional acetylene being added. At the end of this period, the reaction mixture is poured into 4 kg of ice. The organic layer is separated and the aqueous layer extracted twice with 500 ml of chloroform. The combined organic extracts are washed once with 500 ml of water, dried over anhydrous sodium sulfate and concentrated in vacuo. Distillation of the residue yields 142 g of trans-1-chloro-dec-1-en-3-one, ($A_5$, $R_1=C_2H_5$).

b. A solution of 142 g of the product of (a), 140 g of sodium iodide and 500 ml of acetone is refluxed under nitrogen for 4 hours. The acetone is then removed under reduced pressure and the residue dissolved in 500 ml of water. This mixture is extracted twice with 400 ml of ether, the ether extracts combined and washed with 5% aqueous sodium thiosulfate, then with saturated sodium chloride and finally dried over anhydrous sodium sulfate. The ether is removed in vacuo to yield trans-1-iododec-1-en-3-one ($A_4$, $R_1=C_2H_5$).

c. The crude product of (b) is dissolved in 750 ml of benzene, cooled on an ice bath under nitrogen and then treated with 140 ml of 65% sodium bis(2-methoxy ethoxy)aluminium hydride over a one hour period. After stirring an additional 30 minutes at 0° C., 38 ml of concentrated sulfuric acid in 120 ml of water are added to the reaction mixture. The reaction mixture is then filtered and the filtrate washed twice with 500 ml of saturated sodium chloride. The benzene is removed in vacuo and the residue distilled to yield 159 g of dl-trans-1-iodo-3-hydroxy-1-decene, ($A_3$, $R_1=C_2H_5$).

d. A solution of 5.64 g of the product of (c) in 8 ml of isopropenyl methyl ether is cooled to 0° C. and treated with 5 drops of dichloroacetic acid. The ice bath is then removed and the reaction allowed to proceed at room temperature for 1 hour. Five drops of triethyl amine are then added and the excess isopropenyl methyl ether removed in vacuo to yield 7.5 g of dl-trans-1-iodo-3-(2,2-methoxypropoxy)-1-decene, ($A_2$, $R_1=C_2H_5$).

e. 7.5 g of the product of (d) are dissolved in 30 ml of ether and cooled to −78° C. under nitrogen. 32 ml of 1.25 N t-butyl lithium are then added over 30 minutes while maintaining the reaction temperature near −70° C. The reaction mixture is allowed to stir at −78° C. for 45 minutes to yield dl-trans-1-lithio-3-(2,2-methoxypropoxy)-1-decene, ($A_1$, $R_1=C_2H_5$).

f. The thus obtained solution of lithium reagent is added to a solution of 2.60 g of copper pentyne and 7.9 ml of hexamethyl phosphorous triamide in 100 ml of ether, also at −78° C. This mixture is allowed to stir at −78° C. for 15 minutes to yield dl-1-pentynyl-1-[trans-3-(2,2-methoxypropoxy)-1-decenyl]cuprate, (A, $R_1=C_2H_5$).

Similarly, substituting hexanoyl chloride and heptanoyl chloride for octanoyl chloride in step (a), and by following the procedure as described in steps (a) through (f) above, dl-1-pentynyl-1-[trans-3-(2,2-methoxypropoxy)-1-octenyl]cuprate, (A, $R_1=H$), and dl-1-pentynyl-1-[trans-3-(2,2-methoxypropoxy)-1-nonenyl]cuprate, (A, $R_1=CH_3$), are respectively prepared.

PREPARATION 2

This preparation illustrates methods of preparing methyl dl-S-keto-15α(β)-(2,2-methoxypropoxy)-20-ethyl-prost-13(t)-enoate (IV, $R_1=C_2H_5$, $Z=CH_2CH_2$).

In this preparation a solution of 4.0 g of 2-(6-carbomethoxyhexyl)cyclopent-2-en-1-one (B, $Z=CH_2CH_2$) in 10 ml of ether is added to a freshly prepared solution of dl-1-pentynyl-1-[trans-3-(2,2-methoxypropoxy-1-decenyl]cuprate (A, $R_1=C_2H_5$), prepared according to Preparation 1. The reaction mixture is stirred at −78° C. for 1 hour and then poured into 250 ml of ice water. The organic layer is separated and the aqueous layer extracted twice with 100 ml of ether. The combined organic layers are dried over anhydrous sodium sulfate and concentrated in vacuo to yield a mixture of methyl dl-9-keto-15α-(2,2-methoxypropoxy)-20-ethyl-prost-13(t)-enoate and methyl dl-9-keto-15β-(2,2-methoxypropoxy)-20-ethyl-prost-13(t)-enoate.

Similarly, by following the same procedure but replacing dl-1-pentynyl-1-[trans-3-(2,2-methoxypropoxy)-1-decenyl]cuprate by dl-1-pentynyl-1-[trans-3-(2,2-methoxypropoxy)-1-octenyl]cuprate or by dl-1-pentynyl-1-[trans-3-(2,2-methoxypropoxy)-1-nonenyl]cuprate, the following compounds of formula IV:

methyl dl-9-keto-15α-(2,2-methoxypropoxy)-prost-13(t)-enoate and methyl dl-9-keto-15β-(2,2-methoxypropoxy)-prost-13(t)-enoate;

methyl dl-9-keto-15α-(2,2-methoxypropoxy)-20-methyl-prost-13(t)-enoate and methyl dl-9-keto-15β-(2,2-methoxypropoxy)-20-methyl-prost-13(t)-enoate.

In a like manner, substituting 2-(6-carbomethoxy-2-cis-hexenyl)-cyclopent-2-en-1-one for 2-(6-carbomethoxyhexyl)-cyclopent-2-en-1-one yields a mixture of methyl dl-9-keto-15α-(2,2-methoxypropoxy)-20-ethyl-prosta-5(c),13(t)-dienoate and methyl dl-9-keto-15β-(2,2-methoxypropoxy)-20-ethyl-prosta-5(c),13(t)-dienoate.

Similarly, substituting dl-1-pentynyl-1-[trans-3-(2,2-methoxypropoxy)-1-octenyl]cuprate or dl-1-pentynyl-1-[trans-3-(2,2-methoxypropoxy)-1-nonenyl]cuprate and substituting 2-(6-carbomethoxy-2-cis-hexenyl)-cyclopent-2-en-1-one for 2-(6-carbomethoxyhexyl)-cyclopent-2-en-1-one and following the same procedure as described above yields the following compounds respectively: methyl dl-9-keto-15α-(2,2-methoxypropoxy)-prosta-5(c),13(t)-dienoate and methyl dl-9-keto-15β-(2,2-methoxypropoxy)-prosta-5(c),13(t)-dienoate; methyl dl-9-keto-15α-(2,2-methoxypropoxy)-20-methyl-prosta-5(c),13(t)-dienoate and methyl dl-9-keto-15β-(2,2-methoxypropoxy)-20-methyl-prosta-5(c),13(t)-dienoate.

PREPARATION 3

This Preparation illustrates methods for removing the ether protecting group (2,2-methoxypropoxy) from the products of formula IV of Preparation 2. In this preparation, the mixture of methyl dl-9-keto-15α-(2,2-methoxypropoxy)-20-ethyl-prost-13(t)-enoate and methyl dl-9-keto-15β-(2,2-methoxypropoxy)-20-ethyl-prost-13(t)-enoate (IV, $R_{,1}=C_2H_5$, $Z=CH_2CH_2$) obtained in Preparation 2 is dissolved in 50 ml of water, 50 ml of methanol and 20 ml of acetic acid and stirred at room temperature for 1 hour. The reaction mixture is diluted with 100 ml of water and extracted three times with 200 ml of ether. The ether layers are washed with 500 ml of saturated sodium chloride, dried over anhydrous sodium sulfate and concentrated in vacuo. The residue thus obtained is chromatographed on 400 g of silica gel, eluting with 20% ethyl acetate -hexane (v/v), to yield 2.509 g of methyl dl-9-keto-15β-hydroxy-20-ethyl-prost-13(t)-enoate (V, 15β-OH, $R_1=C_2H_5$, $Z=CH_2CH_2$). Further elution with 25% ethyl acetate -hexane yields 2.7 g of methyl dl-9-keto-15α-hydroxy-20-ethyl-prost-13(t)-enoate (V, 15α-OH, $R_1=C_2H_5$, $Z=CH_2CH_2$).

Similarly, by following the same procedure as above, the ether protecting groups are removed from the remaining ether protected products of Preparation 2 to yield the following compounds of formula V which can be separated into the respective isomers by thin-layer preparative chromatography as described above:

methyl dl-9-keto-15α-hydroxy-prost-13(t)-enoate;
methyl dl-9-keto-15β-hydroxy-prost-13(t)-enoate;
methyl dl-9-keto-15α-hydroxy-20-methyl-prost-13(t)-enoate;
methyl dl-9-keto-15β-hydroxy-20-methyl-prost-13(t)-enoate;
methyl dl-9-keto-15α-hydroxy-20-ethyl-prosta-5(c),13(t)-dienoate;
methyl dl-9-keto-15β-hydroxy-20-ethyl-prosta-5(c),13(t)-dienoate;
methyl dl-9-keto-15α-hydroxy-prosta-5(c),13(t)-dienoate;
methyl dl-9-keto-15β-hydroxy-prosta-5(c),13(t)-dienoate;
methyl dl-9-keto-15α-hydroxy-20-methyl-prosta-5(c),13(t)-dienoate
methyl dl-9-keto-15β-hydroxy-20-methyl-prosta-5(c),13(t)-dienoate.

PREPARATION 4

This preparation illustrates methods for preparing methyl dl-9α,15α-dihydroxy-20-ethyl-prost-13(t)-enoate (VI, 15α-OH, 9α-OH, $R_1=C_2H_5$, $Z=CH_2CH_2$), and methyl dl-9β,15α-dihydroxy-20-ethyl-prost-13(t)-enoate (VI, 15α-OH, 9β-OH, $R_1=C_2H_5$, $Z=CH_2CH_2$).

In this preparation, a solution of 1.7 g of methyl dl-9-keto-15α-hydroxy-20-ethyl-prost-13(t)-enoate, prepared according to Preparation 3, in 100 ml of ethanol is cooled on an ice bath and treated with 0.50 g of sodium borohydride. After 45 minutes at 0° C. the reaction is quenched by addition of 1 ml of acetic acid. The reaction mixture is then diluted with 100 ml of water and extracted three times with 200 ml of ethyl acetate. The combined ethyl acetate extracts are washed with saturated aqueous sodium chloride, dried over anhydrous sodium sulfate and concentrated in vacuo. The residue is then chromatographed on 300 g of silica gel. Elution with 25% ethyl acetate/hexane (v/v) yields 425 mg of methyl dl-9α,15α-dihydroxy-20-ethyl-prost-13(t)-enoate. Further elution with 35% ethyl acetate/-hexane yields 1.12 g of methyl dl-9β,15α-dihydroxy-20-ethyl-prost-13(t)-enoate.

In a like manner, substituting the other methyl ester 9-keto-compounds prepared in Preparation 3, i.e., methyl dl-9-keto-15β-hydroxy-20-ethyl-prost-13(t)-enoate;
methyl dl-9-keto-15α-hydroxy-prost-13(t)-enoate;
methyl dl-9-keto-15β-hydroxy-prost-13(t)-enoate;
methyl dl-9-keto-15αhydroxy-20-methyl-prost-13(t)-enoate;
methyl dl-9-keto-15β-hydroxy-20-methyl-prost-13(t)-enoate;
methyl dl-9-keto-15α-hydroxy-20-ethyl prosta-5(c),13(t)-dienoate;
methyl dl-9keto-15β-hydroxy-20-ethyl-prosta-5(c),13(t)-dienoate;
methyl dl-9-keto-b 15α-hydroxy-prosta-5(c),13(t)-dienoate;
methyl dl-9-keto-15β-hydroxy-prosta-5(c),13(t)-dienoate;
methyl dl-9-keto-15α-hydroxy-20-methyl-prosta-5(c),13(t)-dienoate; and
methyl dl-9-keto-15β-hydroxy-20-methyl-prosta-5(c),13(t)-dienoate, for
methyl dl-9-keto-15α-hydroxy-20-ethyl-prost-13(t)-enoate yields the following compounds of formula VI which are separated into the respective isomers by thin-layer preparative chromatography:

methyl dl-9α,15β-dihydroxy-20-ethyl-prost-13(t)-enoate, and
methyl dl-9β,15β-dihydroxy-20-ethyl-prost-13(t)-enoate;
methyl dl-9α,15α-dihydroxy-prost-13(t)-enoate, and
methyl dl-9β,15α-dihydroxy-prost-13(t)-enoate;
methyl dl-9α,15β-dihydroxy-prost-13(t)-enoate, and
methyl dl-9β,15β-dihydroxy-prost-13(t)-enoate;

methyl dl-9α,15α-dihydroxy-20-methyl-prost-13(t)-enoate, and
methyl dl-9β,15α-dihydroxy-20-methyl-prost-13(t)-enoate;
methyl dl-9α,15β-dihydroxy-20-methyl-prost-13(t)-enoate, and
methyl dl-9β,15β-dihydroxy-20-methyl-prost-13(t)-enoate;
methyl dl-9α,15α-dihydroxy-20-ethyl-prosta-5(c),13(t)-dienoate, and
methyl dl-9β,15α-dihydroxy-20-ethyl-prosta-5(c),13(t)-dienoate;
methyl dl-9α,15β-dihydroxy-20-ethyl-prosta-5(c),13(t)-dienoate and
methyl dl-9β,15β-dihydroxy-20-ethyl-prosta-5(c),13(t)-dienoate;
methyl dl-9α,15α-dihydroxy-prosta-5(c),13(t)-dienoate, and
methyl dl-9β,15α-dihydroxy-prosta-5(c),13(t)-dienoate;
methyl dl-9α,15β-dihydroxy-prosta-5(c),13(t)-dienoate, and
methyl dl-9β,15β-dihydroxy-prosta-5(c),13(t)-dienoate;
methyl dl-9α,15α-dihydroxy-20-methyl-prosta-5(c),13(t)-dienoate, and
methyl dl-9β,15α-dihydroxy-20-methyl-prosta-5(c),13(t)-dienoate;
methyl dl-9α,15β-dihydroxy-20-methyl-prosta-5(c),13(t)-dienoate and
methyl dl-9β,15β-dihydroxy-20-methyl-prosta-5(c),13(t)-dienoate.

PREPARATION 5

This preparation illustrates methods for preparing methyl dl-9α-hydroxy-15-keto-20-ethyl-prost-13(t)-enoate (VII, 9α-OH, $R_1=C_2H_5$, $Z=CH_2CH_2$). In this preparation, a solution of 2.006 g of methyl dl-9α,15α-dihydroxy-20-ethyl-prost-13(t)-enoate, prepared according to Preparation 4, in 100 ml of benzene is stirred with 3.5 g of dichlorodicyano quinone for 36 hours at room temperature. The reaction mixture is then diluted with 100 ml of benzene, washed with 100 ml of 5% aqueous sodium bisulfite, 200 ml of saturated aqueous sodium bicarbonate and dried over anhydrous sodium sulfate. The benzene solution is concentrated in vacuo and the residue chromatographed on 300 g of silica gel. Elution with 20% ethyl acetatehexane (v/v) yields 1.188 g of methyl dl-9α-hydroxy-15-keto-20-ethyl-prost-13(t)-enoate.

In a like manner, substituting methyl dl-9α,15β-dihydroxy-20-ethyl-prost-13(t)-enoate for methyl dl-9α,15α-dihydroxy-20-ethyl-prost-13(t)-enoate yields methyl dl-9α-hydroxy-15-keto-20-ethyl-prost-13(t)-enoate.

Likewise, substituting
methyl dl-9β,15α-dihydroxy-20-ethyl-prost-13(t)-enoate or
methyl dl-9β,15β-dihydroxy-20-ethyl-prost-13(t)-enoate;
methyl dl-9α,15α-dihydroxy-prost-13(t)-enoate or
methyl dl-9α,15β-dihydroxy-prost-13(t)-enoate;
methyl dl-9β,15α-dihydroxy-prost-13(t)-enoate or
methyl dl-9β,15βdihydroxy-prost-13(t)-enoate;
methyl dl-9α,15α-dihydroxy-20-methyl-prost-13(t)-enoate or
methyl dl-9α,15β-dihydroxy-20-methyl-prost-13(t)-enoate;
methyl dl-9β,15α-dihydroxy-20-methyl-prost-13(t)-enoate or
methyl dl-9β,15β-dihydroxy-20-methyl-prost-13(t)-enoate,
methyl dl-9α,15α-dihydroxy-20-ethyl-prosta-5(c),13(c),13(t)-dienoate or
methyl dl-9α,15β-dihydroxy-20-ethyl-prosta-5(c),13(t)-dienoate;
methyl dl-9β,15α-dihydroxy-20-ethyl-prosta-5(c),13(t)-dienoate or
methyl dl-9β,15β-dihydroxy-20-ethyl-prosta-5(c),13(t)-dienoate;
methyl dl-9α,15α-dihydroxy-prosta-5(c),13(t)-dienoate or
methyl dl-9α,15β-dihydroxy-prosta-5(c),13(t)-dienoate;
methyl dl-9β,15α-dihydroxy-prosta-5(c),13(t)-dienoate or
methyl dl-9β,15β-dihydroxy-prosta-5(c),13(t)-dienoate;
methyl dl-9α,15α-dihydroxy-20-methyl-prosta-5(c),13(t)-dienoate or
methyl dl-9α,15β-dihydroxy-20-methyl-prosta-5(c),13(t)-dienoate;
methyl dl-9β,15α-dihydroxy-20-methyl-prosta-5(c),13(t)-dienoate or methyl dl-9β,15β-dihydroxy-20-methyl-prosta-5(c),13(t)-dienoate;

respectively, for methyl dl-9α,15α-dihydroxy-20-ethyl-prost-13(t)-enoate as starting materials yields the following compounds of formula VII:
methyl dl-9β-hydroxy-15-keto-20-ethyl-prost-13(t)-enoate;
methyl dl-9α-hydroxy-15-keto-prost-13(t)-enoate;
methyl dl-9β-hydroxy-15-keto-prost-13(t)-enoate;
methyl dl-9α-hydroxy-15-keto-20-methyl-prost-13(t)-enoate;
methyl dl-9β-hydroxy-15-keto-20-methyl-prost-13(t)-enoate;
methyl dl-9α-hydroxy-15-keto-20-ethyl-prosta-5(c),13(t)-dienoate;
methyl dl-9β-hydroxy-15-keto-20-ethyl-prosta-5(c),13(t)-dienoate;
methyl dl-9α-hydroxy-15-keto-prosta-5(c),13(t)-dienoate;
methyl dl-9β-hydroxy-15-keto-prosta-5(c),13(t)-dienoate;
methyl dl-9α-hydroxy-15-keto-20-methyl-prosta-5(c),13(t)-dienoate; and
methyl dl-9β-hydroxy-15-keto-20-methyl-prosta-5(c),13(t)-dienoate; respectively.

PREPARATION 6

This preparation illustrates methods for preparing methyl dl-9α,15α-dihydroxy-15β-methyl-20-ethyl-prost-13(t)-enoate (VIII, 9α-OH, 15α-OH, 5β-$CH_3$, $R_1=C_2H_5$, $Z=CH_2CH_2$), and its isomer methyl dl-9α,15β-dihydroxy-15α-methyl-20-ethyl-prost-13(t)-enoate, (VIII, 9α-OH, 15β-OH, 15α-$CH_3$, $R_1=C_2H_5$, $Z=CH_2CH_2$).

In this preparation, a solution of 1.188 g of methyl dl-9α-hydroxy-15-keto-20-ethyl-prost-13(t)-enoate, prepared according to Preparation 5, in 70 ml of tetrahydrofuran is cooled to −30° C. and treated with 6.0 ml of 3 N methyl magnesium bromide in tetrahydrofuran. After stirring for 45 minutes at −30° C., the reaction is quenched by the addition of 3 ml of acetone and then poured into 200 ml of ice water. The aqueous solution is then extracted three times with 65 ml of ethyl acetate and the combined ethyl acetate extracts washed with 300 ml of saturated aqueous sodium chloride. The organic layer is then dried over anhydrous sodium sulfate and concentrated in vacuo. The thus-obtained residue is chromatographed on 350 g of silica gel. Elution with 20% ethyl acetate - hexane (v/v) yields 0.511 g of methyl dl-9α,15β-dihydroxy-15α-methyl-20-ethyl-prost-13(t)-enoate. Further elution with 25% ethyl acetate - hexane (v/v) yields 0.454 g of methyl dl-9α,15α-dihydroxy-15β-methyl-20-ethyl-prost-13(t)-enoate.

In a like manner, substituting methyl dl-9β-hydroxy-15-keto-20-ethyl-prost-13(t)-enoate;
methyl dl-9α-hydroxy-15-keto-prost-13(t)-enoate;
methyl dl-9β-hydroxy-15-keto-prost-13(t)-enoate;
methyl dl-9α-hydroxy-15-keto-20-methyl-prost-13(t)-enoate;
methyl dl-9β-hydroxy-15-keto-20-methyl-prost-13(t)-enoate;
methyl dl-9α-hydroxy-15-keto-20-ethyl-prosta-5(c),13(t)-dienoate;
methyl dl-9β-hydroxy-15-keto-20-ethyl-prosta-5(c),13(t)-dienoate;
methyl dl-9α-hydroxy-15-keto-prosta-5(c),13(t)-dienoate;
methyl dl-9β-hydroxy-15-keto-prosta-5(c),13(t)-dienoate;
methyl dl-9α-hydroxy-15-keto-20-methyl-prosta-5(c),13(t)-dienoate; and
methyl dl-9β-hydroxy-15-keto-20-methyl-prosta-5(c),13(t)-dienoate for methyl dl-9α-hydroxy-15-keto-20-ethyl-prost-13(t)-enoate and following the procedure as described above, yields the following pair of compounds of formula VIII respectively, which are separated by thin-layer chromatography:

methyl dl-9β,15α-dihydroxy-5β-methyl-20-ethyl-prost-13(t)-enoate and
methyl dl-9β,15β-dihydroxy-15α-methyl-20-ethyl-prost-13(t)-enoate;
methyl dl-9α,15α-dihydroxy-15β-methyl-prost-13(t)-enoate and
methyl dl-9α,15β-dihydroxy-15α-methyl-prost-13(t)-enoate;
methyl dl-9β,15α-dihydroxy-15β-methyl-prost-13(t)-enoate and
methyl dl-9β,15β-dihydroxy-15α-methyl-prost-13(t)-enoate;
methyl dl-9α,15α-dihydroxy-15β-methyl-20-methyl-prost-13(t)-enoate and
methyl dl-9α,15β-dihydroxy-15α-methyl-20-methyl-prost-13(t)-enoate;
methyl dl-9β,15α-dihydroxy-15β-methyl-20-methyl-prost-13(t)-enoate and
methyl dl-9β,15β-dihydroxy-15α-methyl-20-methyl-prost-13(t)-enoate;
methyl dl-9α,15α-dihydroxy-15β-methyl-20-ethyl-prosta-5(c),13(t)-dienoate and
methyl dl-9α,15β-dihydroxy-15α-methyl-20-ethyl-prosta-5(c),13(t)-dienoate;
methyl dl-9β,15α-dihydroxy-15β-methyl-20-ethyl-prosta-5(c),13(t)-dienoate and
methyl dl-9β,15β-dihydroxy-15α-methyl-20-ethyl-prosta-5(c),13(t)-dienoate;
methyl dl-9α,15α-dihydroxy-15β-methyl-prosta-5(c),13(t)-dienoate and
methyl dl-9α,15β-dihydroxy-15α-methyl-prosta-5(c),13(t)-dienoate;
methyl dl-9β,15α-dihydroxy-15β-methyl-prosta-5(c),13(t)-dienoate and
methyl dl-9β,15β-dihydroxy-15α-methyl-prosta-5(c),13(t)-dienoate;
methyl dl-9α,15α-dihydroxy-15β-methyl-20-methyl-prosta-5(c),13(t)-dienoate and
methyl dl-9α,15β-dihydroxy-15α-methyl-20-methyl-prosta-5(c),13(t)-dienoate;
methyl dl-9β,15α-dihydroxy-15β-methyl-20-methyl-prosta-5(c),13(t)-dienoate and
methyl dl-9β,15β-dihydroxy-15α-methyl-20-methyl-prosta-5(c),13(t)-dienoate.

PREPARATION 7

This preparation illustrates methods for preparing methyl dl-9-keto-15α-hydroxy-15β-methyl-20-ethyl-prost-13(t)-enoate (IX, 15α-OH, 15β-$CH_3$, $R_1$=$C_2H_5$, Z=$CH_2CH_2$).

In this preparation, a suspension of 1.00 g of Celite (diatomaceous earth), 1.60 g of chromium trioxide and 53 ml of anhydrous methylene chloride is stirred under nitrogen while 2.29 g of pyridine are added. The resulting suspension is stirred at room temperature for 30 minutes. A solution of 0.94 g of methyl dl-9α,15α-dihydroxy-15β-methyl-20-ethyl-prost-13(t)-enoate prepared according to Preparation 6, in 5 ml of methylene chloride is added. After 30 minutes at room temperature, the reaction mixture is filtered through 50 g of alumina. The alumina is washed several times with methylene chloride and the combined filtrates concentrated under reduced pressure to yield 0.76 g of methyl dl-9-keto-15α-hydroxy-15β-methyl-20-ethyl-prost-13(t)-enoate.

Similarly, substituting methyl dl-9β,15α-dihydroxy-15β-methyl-20-ethyl-prost-13(t)-enoate for methyl dl-9α,15α-dihydroxy-15β-methyl-20-ethyl-prost-13(t)-enoate yields methyl dl-9-keto-15α-hydroxy-15β-methyl-20-ethyl-prost-13(t)-enoate.

In a like manner, substituting methyl dl-9α,15β-dihydroxy-15α-methyl-20-ethyl-prost-13(t)-enoate or
methyl dl-9β,15β-dihydroxy-15α-methyl-20-ethyl-prost-13(t)-enoate;
methyl dl-9α,15β-dihydroxy-5α-methyl-prost-13(t)-enoate or
methyl dl-9β,15β-dihydroxy-15α-methyl-prost-13(t)-enoate;
methyl dl-9α,15α-dihydroxy-15β-methyl-prost-13(t)-enoate or
methyl dl-9β,15α-dihydroxy-15β-methyl-prost-13(t)-enoate;
methyl dl-9α,15β-dihydroxy-15α-methyl-20-methyl-prost-13(t)-enoate or
methyl dl-9β,15β-dihydroxy-15α-methyl-20-methyl-prost-13(t)-enoate;
methyl dl-9α,15α-dihydroxy-15β-methyl-20-methyl-prost-13(t)-enoate or
methyl dl-9β,15α-dihydroxy-15β-methyl-20-methyl-prost-13(t)-enoate;
methyl dl-9α,15β-dihydroxy-15α-methyl-20-ethyl-prosta-5(c),13(t)-dienoate or
methyl dl-9β,15β-dihydroxy-15α-methyl-20-ethyl-prosta-5(c),13(t)-dienoate;
methyl dl-9α,15α-dihydroxy-15β-methyl-20-ethyl-prosta-5(c),13(t)-dienoate or
methyl dl-9β,15α-dihydroxy-15β-methyl-20-ethyl-prosta-5(c),13(t)-dienoate;

methyl dl-9α,15β-dihydroxy-15α-methyl-prosta-5(c),13(t)-dienoate or
methyl dl-9β,15β-dihydroxy-15α-methyl-prosta-5(c),13(t)-dienoate;
methyl dl-9α,15α-dihydroxy-15β-methyl-prosta-5(c),13(t)-dienoate or
methyl dl-9β,15α-dihydroxy-15β-methyl-prosta-5(c),13(t)-dienoate;
methyl dl-9α,15β-dihydroxy-15α-methyl-20-methyl-prosta-5(c),13(t)-dienoate or
methyl dl-9β,15β-dihydroxy-15α-methyl-20-methyl-prosta-5(c),13(t)-dienoate.
methyl dl-9α,15α-dihydroxy-15β-methyl-20-methyl-prosta-5(c),13(t)-dienoate or
methyl dl-9β,15α-dihydroxy-15β-methyl-20-methyl-prosta-5(c),13(t)-dienoate;

respectively for methyl dl-9α,15α-dihydroxy-15β-methyl-20-ethyl-prost-13(t)-enoate as starting material and following the procedure described above yields the compounds of formula IX listed herebelow:

methyl dl-9-keto-15β-hydroxy-15α-methyl-20-ethyl-prost-13(t)-enoate;
methyl dl-9-keto-15β-hydroxy-15α-methyl-prost-13(t)-enoate;
methyl dl-9-keto-15α-hydroxy-15β-methyl-prost-13(t)-enoate;
methyl dl-9-keto-15β-hydroxy-15α-methyl-20-methyl-prost-13(t)-enoate;
methyl dl-9-keto-15α-hydroxy-15β-methyl-20-methyl-prost-13(t)-enoate;
methyl dl-9-keto-15β-hydroxy-15α-methyl-20-ethyl-prosta-5(c),13(t)-dienoate;
methyl dl-9-keto-15α-hydroxy-15β-methyl-20-ethyl-prosta-5(c),13(t)-dienoate;
methyl dl-9-keto-15β-hydroxy-15α-methyl-prosta-5(c),13(t)-dienoate;
methyl dl-9-keto-15α-hydroxy-15β-methyl-prosta-5(c),13(t)-dienoate;
methyl dl-9-keto-15β-hydroxy-15α-methyl-20-methyl-prosta-5(c),13(t)-dienoate; and
methyl dl-9-keto-15α-hydroxy-15β-methyl-20-methyl-prosta-5(c),13(t)-dienoate;

respectively.

PREPARATION 8

This preparation illustrates methods for preparing dl-9α,15α-dihydroxy-15β-methyl-20-ethyl-prost-13(t)-enoic acid, (VIII, 9α-OH, 15α-OH, 15β-$CH_3$, free acid, $R_1$=$C_2H_5$, Z=$CH_2CH_2$).

In this preparation, a solution of 0.454 g of methyl dl-9α,15α-dihydroxy-15β-methyl-20-ethyl-prost-13(t)-enoate, prepared according to Preparation 6, 0.75 g of potassium hydroxide, 10 ml of methanol and 10 ml of water is stirred at room temperature under nitrogen for 1 hour and 45 minutes. The reaction mixture is diluted with 50 ml of water and washed with 100 ml of ether. The aqueous layer is then acified to pH 4 with 1 N hydrochloric acid, saturated with sodium chloride, and extracted three times with 75 ml of ethyl acetate. The combined ethyl acetate extracts are washed with 300 ml of saturated aqueous sodium chloride and dried over anhydrous sodium sulfate. Concentration of the organic solution gives a residue which is recrystallized from 1 ml of ethyl acetate and 10 ml of hexane. On cooling overnight at −20° C., 0.329 g of dl-9α,15α-dihydroxy-15β-methyl-20-ethyl-prost-13(t)-enoic acid precipitates and is collected by filtration.

Similarly, substituting the other compounds obtained in Preparation 6 for methyl dl-9α,15α-dihydroxy-15β-methyl-20-ethyl-prost-13(t)-enoate and following the procedure as described above yields the following free acids, corresponding to compounds of formula VIII:

dl-9α,15β-dihydroxy-15α-methyl-20-ethyl-prost-13(t)-enoic acid;
dl-9β,15α-dihydroxy-15β-methyl-20-ethyl-prost-13(t)-enoic acid;
dl-9β,15β-dihydroxy-15α-methyl-29-ethyl-prost-13(t)-enoic acid;
dl-9α,15α-dihydroxy-15β-methyl-prost-13(t)-enoic acid;
dl-9α,15β-dihydroxy-15α-methyl-prost-13(t)-enoic acid;
dl-9β,15α-dihydroxy-15β-methyl-prost-13(t)-enoic acid;
dl-9β,15β-dihydroxy-15α-methyl-prost-13(t)-enoic acid;
dl-9α,15α-dihydroxy-15β-methyl-20-methyl-prost-13(t)-enoic acid;
dl-9α,15β-dihydroxy-15α-methyl-20-methyl-prost-13(t)-enoic acid;
dl-9β,15α-dihydroxy-15β-methyl-20-methyl-prost-13(t)-enoic acid;
dl-9β,15β-dihydroxy-15α-methyl-20-methyl-prost-13(t)-enoic acid;
dl-9α,15α-dihydroxy-15β-methyl-20-ethyl-prosta-5(c),13(t)-dienoic acid;
dl-9α,15β-dihydroxy-15α-methyl-29-ethyl-prosta-5(c),13(t)-dienoic acid;
dl-9β,15α-dihydroxy-15β-methyl-20-ethyl-prosta-5(c),13(t)-dienoic acid;
dl-9β,15β-dihydroxy-15α-methyl-20-ethyl-prosta-5(c),13(t)-dienoic acid;
dl-9α,15α-dihydroxy-15β-methyl-prosta-5(c),13(t)-dienoic acid;
dl-9α,15β-dihydroxy-15α-methyl-prosta-5(c),13(t)-dienoic acid;
dl-9β,15α-dihydroxy-15β-methyl-prosta-5(c),13(t)-dienoic acid;
dl-9β,15β-dihydroxy-15α-methyl-prosta-5(c),13(t)-dienoic acid;
dl-9α,15α-dihydroxy-15β-methyl-20-methyl-prosta-5(c),13(t)-dienoic acid;
dl-9α,15β-dihydroxy-15α-methyl-prosta-5(c),13(t)-dienoic acid;
dl-9β,15α-dihydroxy-15β-methyl-20-methyl-prosta-5(c),13(t)-dienoic acid; and
dl-9β,15β-dihydroxy-15α-methyl-20-methyl-prosta-5(c),13(t)-dienoic acid.

In a like manner, substituting the compounds prepared in Preparation 7 for methyl-dl-9α,15α-dihydroxy-15β-methyl-20-ethyl-prost-13(t)-enoate and following the procedure as described above yields the following free acids, corresponding to compounds of formula IX:

dl-9-keto-15α-hydroxy-15β-methyl-20-ethyl-prost-13(t)-enoic acid;
dl-9-keto-15β-hydroxy-15α-methyl-20-ethyl-prost-13(t)-enoic acid;
dl-9-keto-15α-hydroxy-15β-methyl-prost-13(t)-enoic acid;
dl-9-keto-15β-hydroxy-15α-methyl-prost-13(t)-enoic acid;
dl-9-keto-15α-hydroxy-15β-methyl-20-methyl-prost-13(t)-enoic acid;
dl-9-keto-15β-hydroxy-15α-methyl-20-methyl-prost-13(t)-enoic acid;

dl-9-keto-15α-hydroxy-15β-methyl-20-ethyl-prosta-5(c),13(t)-dienoic acid;
dl-9-keto-15β-hydroxy-15α-methyl-20-ethyl-prosta-5(c),13(t)-dienoic acid;
dl-9-keto-15α-hydroxy-15β-methyl-prosta-5(c),13(t)-dienoic acid;
dl-9-keto-15β-hydroxy-15α-methyl-prosta-5(c),13(t)-dienoic acid;
dl-9-keto-15α-hydroxy-15β-methyl-20-methyl-prosta-5(c),13(t)-dienoic acid; and
dl-9-keto-15β-hydroxy-15α-methyl-20-prosta-5(c),13(t)-dienoic acid.

Also, substituting the compounds prepared in Preparation 4 for methyl dl-9α,15α-dihydroxy-15β-methyl-20-ethyl-prost-13(t)-enoate and following the procedure as described above yields the following free acids, corresponding to compounds of formula VI:

dl-9α,15α-dihydroxy-20-ethyl-prost-13(t)-enoic acid;
dl-9β,15α-dihydroxy-20-ethyl-prost-13(t)-enoic acid;
dl-9α,15β-dihydroxy-20-ethyl-prost-13(t)-enoic acid;
dl-9β,15β-dihydroxy-20-ethyl-prost-13(t)-enoic acid;
dl-9α,15α-dihydroxy-prost-13(t)-enoic acid;
dl-9β,15α-dihydroxy-prost-13(t)-enoic acid;
dl-9α,15β-dihydroxy-prost-13(t)-enoic acid;
dl-9β,15β-dihydroxy-prost-13(t)-enoic acid;
dl-9α,15α-dihydroxy-20-methyl-prost-13(t)-enoic acid;
dl-9β,15α-dihydroxy-20-methyl-prost-13(t)-enoic acid;
dl-9α,15β-dihydroxy-20-methyl-prost-13(t)-enoic acid;
dl-9β,15β-dihydroxy-20-methyl-prost-13(t)-enoic acid;
dl-9α,15α-dihydroxy-20-ethyl-prost-5(c),13(t)-dienoic acid;
dl-9β,15α-dihydroxy-20-ethyl-prosta-5(c),13(t)-dienoic acid;
dl-9α,15β-dihydroxy-20-ethyl-prosta-5(c),13(t)-dienoic acid;
dl-9β,15β-dihydroxy-20-ethyl-prosta-5(c),13(t)-dienoic acid;
dl-9α,15α-dihydroxy-prosta-5(c),13(t)-dienoic acid;
dl-9β,15α-dihydroxy-prosta-5(c),13(t)-dienoic acid;
dl-9α,15β-dihydroxy-prosta-5(c),13(t)-dienoic acid;
dl-9α,15α-dihydroxy-prosta-5(c),13(t)-dienoic acid;
dl-9α,15α-dihydroxy-20-methyl-prosta-5(c),13(t)-dienoic acid;
dl-9β,15α-dihydroxy-20-methyl-prosta-5(c),13(t)-dienoic acid;
dl-9α,15β-dihydroxy-20-methyl-prosta-5(c),13(t)-dienoic acid; and
dl-9β,15β-dihydroxy-20-methyl-prosta-5(c),13(t)-dienoic acid:

Similarly, substituting the compounds prepared in Preparation 3 for methyl dl-9α,15α-dihydroxy-15β-methyl-20-ethyl-prost-13(t)-enoate and following the procedure as described above yields the following free acids, corresponding to compounds of formula V:

dl-9-keto-15α-hydroxy-20-ethyl-prost-13(t)-enoic acid;
dl-9-keto-15β-hydroxy-20-ethyl-prost-13(t)-enoic acid;
dl-9-keto-15α-hydroxy-prost-13(t)-enoic acid;
dl-9-keto-15β-hydroxy-prost-13(t)-enoic acid;
dl-9-keto-15α-hydroxy-20-methyl-prost-13(t)-enoic acid;
dl-9-keto-15β-hydroxy-20-methyl-prost-13(t)-enoic acid;
dl-9-keto-15α-hydroxy-20-ethyl-prosta-5(c),13(t)-dienoic acid;
dl-9-keto-15β-hydroxy-20-ethyl-prosta-5(c),13(t)-dienoic acid;
dl-9-keto-15α-hydroxy-prosta-5(c),13(t)-dienoic acid;
dl-9-keto-15β-hydroxy-prosta-5(c),13(t)-dienoic acid;
dl-9-keto-15α-hydroxy-20-methyl-prosta-5(c),13(t)-dienoic acid and
dl-9-keto-15β-hydroxy-20-methyl-prosta-5(c),13(t)-dienoic acid;

In this Application use is made of the microbiological Classification according to the scheme proposed by Ainsworth (1966):

"A general purpose classification of fungi—Bibliography of Systematic Mycology (1966), 1–4—Commonwealth Mycological Institute—Kew, Surrey", and use is made of Ainsworth and Bibsy's Dictionary of the Fungi 6th edition (1971).

The aforesaid Division of Eumycota embraces 5 Sub-divisions, viz. Mastigomycotina, Deuteromycotina, Basidiomycotina, Ascomycotina and Zygomycotina. While numerous species of microorganisms falling within the 5 Sub-divisions of Eumycota can be employed in the process of the invention for the preparation of the 18ξ, 19ξ- and 20ξ-hydroxy-prostaglandin derivatives of formula I supra, it is preferred to employ species of microorganisms falling within the Classes and Orders listed hereinbelow:

- Matigomycotina
  - Oomycetes
    - Saprolegniales
    - Peronosporales
- Deuteromycotina
  - Coelomycetes
    - Sphaeropsidales
    - Melanconiales
  - Hyphomycetes
    - Hyphomycetales
    - Tuberculariales
- Basidiomycotina
  - Gasteromycetes
    - Lycoperdales
  - Hymenomycetes
    - Aphyllophorales
    - Agaricales
- Ascomycotina
  - Plectomycetes
    - Eurotiales
    - Microascales
  - Pyrenomycetes
    - Sphaeriales
    - Hypocreales
  - Loculoascomycetes
    - Pleosporales
- Zygomycotina
  - Zygomycetes
    - Mucorales
    - Entomophthorales While numerous species of microorganisms falling within the Family of Streptomycetaceae can be employed in the process of the invention for the preparation of the 18ξ- and 19ξ-hydroxy-prostaglandin derivatives of general formula I, it is preferred to employ species of microorganisms falling within the genus Streptomyces.

Cultures of a large number of species, falling within the group of microorganisms which can be employed in the process of the invention, are available from known sources, such as:

"Centraal Bureau voor Schimmelcultures" (CBS), Baarn, The Neatherlands;

"American Type Culture Collection" (ATCC), Rockville, Maryland, U.S.A.;

"Northern Utilization Research and Development Division of U.S. Department of Agriculture" (NRRL), Peoria, Illinois, U.S.A. and "Commonwealth Mycological Institute" (CMI), Kew, Surrey, England.

The microorganisms to be used is grown in the conventional way, preferably in a liquid medium with constant aeration by shaking or by stirring while passing through air. Culture media used for the growth of fungal organisms and Streptomyces are well known in the art and principally consist of (1) a source of carbon such as glucose, maltose, sucrose, starch, dextrine and vegetable oils and (2) a source of nitrogen such as ammonia salts, meat and fish flours, corn steep solids and other nutritive substances containing nitrogen, (3) inorganic salts such as sodium, potassium, magnesium, sulphates, phosphates and chlorides, and, opttionally, trace elements. The foregoing materials are added in the desired amounts to a quantity of tap water, and the solution is sterilized prior to inoculation with the microorganism culture.

The prostaglandin or prostaglandin derivative of general formula II to be hydroxylated is added in the form of a fine crystal suspension or dissolved in a solvent such as acetone, ethanol or dimethyl formamide. During the incubation of the starting prostaglandin with the fungus or streptomycete cultures, aeration is provided by shaking and the temperature is kept between 20° and 40° C. during 12-hours. The hydroxylation is followed with the aid of thin-layer chromatography. The hydroxylated products are isolated from the fermentation broth by known procedures. At the end of the fermentation the broth is filtered, the filtrate acidified to about ph=3 and extracted with a suitable organic solvent. For acidification either organic or mineral acids can be used, such as phosphoric acid, sulphuric acid, formic acid, and citric acid. Extraction can be carried out at pH between 1 and 5. However, it is advisable not to work at pH lower than 2, as many prostaglandin derivatives are acid sensitive. Suitable solvents for extraction are ketones, esters and ethers, such as methyl isobutyl ketone, ethyl acetate and diethyl ether. It is also possible to acidify the culture broth and extract directly without filtration.

The crude products are purified by known procedures such as direct crystallisation or column chromatography. A suitable adsorbent is for example silica gel. The silica is normally pre-treated with 20% of water containing 1% of acetic acid and the column eluted with suitable organic solvents or mixtures thereof, such as ethyl acetate - heptane (8.3 v/v) containing 0.1% of acetic acid.

The analysis of the products thus obtained sometimes presents some difficulty. Mass spectrometry of prostaglandins often yields complex spectra, which are difficult to interpret. Sometimes even the molecular peak cannot be determined.

Better results are obtained by protecting reactive groups such as hydroxyl groups, keto groups and carboxylic groups by the following reactions, respectively:

1. esterification of the carboxylic groups by diazomethane;
2. transformation of keto groups into methoximes; and
3. conversion of hydroxyl groups into trimethylsilyloxy groups, for example with N,O-bis(trimethylsilyl) trifluoro-acetamide.

Such converted products are hereinafter referred to as "protected products". The crude derivative is then injected into a GLC-column connected to a double focussing mass spectrometer and the spectrum of the largest GLC-peak is recorded. GLC is used to obtain a separation of main products from byproducts and to record C-values according to the method of S. Bergstrom et al., J. Biol. Chem.-238 (1963), 3555.

For the determination of these values mixtures of normal-fatty acids are used as standards. The retention times of the standards are plotted on a logarithmic scale against the number of carbon atoms of the acids on a linear scale. These diagrams are then used to convert observed retention times to C-values.

These C-values are obtained using the following gas-chromatographic conditions:

Column: 5 ft, 2.3 mm i.d.

Stationary phase: 3% OV-17 on Gaschrom Q 100–120 mesh

Oven temperature: 235° C.

Carrier gas: 38 ml $N_2$/min.

The 18ξ-hydroxy and 19ξ-hydroxy-prostaglandin derivatives are usually obtained as a mixture; the isomers can be separated from each other and each of the isomers isolated according to the procedures described hereinabove. Sometimes also 17ξ-hydroxylated products are obtained as byproducts. These 17ξ-hydroxy-prostaglandin derivatives are also novel compounds. The hydroxylation of $PGA_2$ is usually preceded by reduction of the 10(11) double bond.

The alkyl esters are obtained by treatment of the compounds of general formula I with an excess of a diazoalkane such as diazomethane, diazoethane or diazopropane in diethyl ether or methylene chloride solution, in a conventional manner.

Alternatively, the mixture of 18ξ- and 19ξ-hydroxylated compounds can be esterified as described immediately above, and the 18ξ-hydroxy and 19ξ-hydroxyalkyl esters recovered, purified and/or separated, according to procedures described above for the compounds of formula I.

The salt derivatives of the acids of formula I are prepared by treating the corresponding free acids with about one molar equivalent of a suitable base, such as sodium hydroxide, potassium hydroxide, ammonium hydroxide, calcium hydroxide, trimethylamine, triethylamine, tripropylamine, β-(dimethylamino) ethanol, β-(diethylamino) ethanol. triethanolamine, arginine, lysine, caffeine, procaine and the like. The reaction is usually conducted in an aqueous solution, alone or in combination with an inert, water-miscible organic solvent, at a temperature of from about 0° C. to about 30° C., preferably at room temperature. Typical inert, water-miscible organic solvents include methanol, ethanol, isopropanol, butanol, dioxane or tetrahydrofuran. When divalent metal salts are prepared, such as the calcium salts or magnesium salts, the free acid starting material is treated with at least one half molar equivalent of the base.

The free acids, esters or salts of the 18ξ-, 19ξ- and 20 -hydroxy-prostaglandin derivatives of general formula I can be administered in a wide variety of dosage forms, either alone or in combination with other pharmaceutical compatible medicaments, in the form of pharmaceutical compositions suited for oral or parenteral administration of inhalation. The compounds are typically administered as pharmaceutical compositions consisting essentially of the free acids, esters or salts of the invention, and a pharmaceutical carrier. The pharmaceutical carrier can be either a solid material, liquid or aerosol, in which the free acid, ester or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the free acids, esters or salts can, for example, be administered as an aerosol in an inert propellant together with a cosolvent, e.g., ethanol, together with optional preservatives, surfactants, stabilizers, isotonic and buffering agents. Additional general information concerning the inhalation administration of aerosols can be had by reference to U.S. Pat. Nos. 2,868,691 and 3,095,355.

For the preparation of an aerosol the active compound is first micronized; preferred particle size is from 0.5 to 10$\mu$. The solutions or suspensions to be used contain from 0.02 to 0.5 mg of active compound per ml of pharmaceutically acceptable solvent medium. Preferably, the pH of the solution or suspension is between 4 and 7.

The solutions or suspensions are used in an aerosol container provided with a metered valve which releases preferably from 50 to 60 $\mu$l per puff. Propellants conventional in pharmaceutical aerosols, such as various chloro-fluoro-alkanes, may be used.

A suitable aerosol can be prepared, for example, using solutions or suspensions and propellants consisting of:

| | |
|---|---|
| 9-keto-11α,15α,19ξ-trihydroxy-prost-13(t)-enoic acid triethanolamine salt | 0.25% |
| ethanol absolute | 36.75% |
| dichlorodifluoromethane/1,2-dichloro-1,1,2,2-tetrafluoroethane (40/60) ad | 100% |
| or | |
| 9-keto-11α,15α,18ξ-trihydroxy-prost-13(t)-enoic acid | 0.5 g |
| propylene glycol | 1 g |
| ethanol absolute | 19.5 g |
| dichlorodifluoromethane/1,2-dichloro-1,1,2,2-tetrafluoroethane (40/60) ad | 100 g |

The free acids, esters or salts of the invention are typically administered i.v. in dosages of about 0.1 to 10 mg and p.o. in dosages of about 1 to 100 mg. The daily doses are i.v. about 0.4 to 40 mg and p.o. about 6 to 600 mg.

The following Examples illustrate the invention.

EXAMPLE I a. An agar slant of Thozetellopsis tocklaiensis (CBS 378.58) was used to inoculate 100 ml of sterile 20–20 medium in a 500 ml conical flask. This medium was prepared by solving 20 g of glucose in 500 ml of tap water, adding 20 g of corn steep solids and filling up to 1 liter with tap water; pH was adjusted to 6.5 with the aid of a 30% solution of sodium hydroxide. Sterilization was effected during 20 minutes at 120° C.

The flask was incubated during 72 hours at 26° C. on a rotary shaker (280 r.p.m., 2.5 cm stroke). From the culture obtained 5 ml were used to inoculate 10 ml of sterile 10–10 medium in a 500 ml conical flask. The medium was prepared as the 20–20 medium described above using 10 g of glucose and corn steep solids each per liter. The flask was incubated at 26° C. on the rotary shaker.

18 Hours after inoculation 20 mg of dl-9-keto-15αhydroxy-prost-13(t)-enoic acid, prepared according to Preparations 3 and 8, dissolved in 2.5 ml of 50% aqueous ethanol, were added and the incubation was continued for another 24 hours at 26° C. Hereafter the culture broth was filtered, the filtrate acidified to pH=3 with a 10% aqueous citric acid solution, and extracted three times with 20 ml of ethyl acetate. The extract was evaporated in vacuo and the residue purified by column chromatography ($SiO_2$ pretreated with 1% acetic acid; eluted with ethyl acetate - heptane (8:3) containing 0.1% acetic acid). The matching fractions were combined and evaporated in vacuo yielding 2.5 mg of 9-keto-15α, 18ξ-dihydroxy-prost-13(t)-enoic acid and 3.5mg of 9keto-15α, 19ξ-dihydroxy-prost-13(t)-enoic acid.

The protected 18-hydroxy product (silyl ether, methoxime, methyl ester) has:

C-value: 25.9

Molecular peak in mass spectrum: m/e=541

Intense peaks: 510, 420, 382, 309, 197, 131, 129.

Minor characteristic fragments: 422, 390, 364, 222, 144.

The protected 19-hydroxy product has:

C-value: 26.2

Molecular peak in mass spectrum: m/e=541

Intense peaks: 510, 420, 382, 129, 117.

Minor characteristic fragments: 466, 368, 330, 309, 222, 143.

b. In the same way dl-9-keto-15β-hydroxy-prost-13(t)-enoic acid, prepared according to Preparations 3 and 8, was converted into 9-keto-15β, 18ξ-dihydroxy-prost-13(t)-enoic acid and 9-keto-15β, 19ξ-dihydroxy-prost-13(t)-enoic acid.

The protected 18-hydroxy product has:

C-value: 26.0

Molecular peak in mass spectrum: m/e=541

Intense peaks: 510, 420, 382, 309, 197, 131, 129.

Minor characteristic fragments: 422, 390, 364, 222, 144.

The protected 19-hydroxy product has:

C-value: 26.3

Molecular peak in mass spectrum: m/e=541

Intense peaks: 510, 420, 382, 129, 117.

Minor characteristic fragments: 466, 368, 330, 309, 222, 143 c. In the same way dl-9α,15β-dihydroxy-prost-13(t)-enoic acid, prepared according to Preparations 4 and 8, was converted into 9α,15β, 18ξ-trihydroxy-prost-13(t)-enoic acid and 9α,15β19ξ-trihydroxy-prost-13(t)-enoic acid. The silylated methyl ester of the 18-hydroxy compound has:

C-value: 24.3

Molecular peak in mass spectrum: m/e=586

Intense peaks: 427, 337, 297, 197, 131, 129.

Minor characteristic fragments: 557, 496, 467, 377, 350, 310, 247, 144.

The silylated methyl ester of the 19-hydroxy compound has:

C-value: 24.6

Molecular peak in mass spectrum: m/e=586

Intense peaks: 427, 337, 297, 197, 143, 129, 117.

Minor characteristic fragments: 496, 452, 310, 247, 143.

d. In the same way dl-9β,15β-dihydroxy-prost-13(t)-enoic acid, prepared according to Preparations 4 and 8, was converted into 9β, 15β, 18ξ-trihydroxy-prost-13(t)-enoic acid and 9β, 15β, 19ξ-trihydroxy-prost-13(t)-enoic acid. The silylated methyl ester of the 18-hydroxy compound has:

C-value: 24.3

Molecular peak in mass spectrum: m/e=586

Intense peaks: 427, 337, 247, 197, 131, 129.

Minor characteristic fragments: 557, 467, 377, 350, 297, 223.

The silylated methyl ester of the 19-hydroxy compound has:

C-value: 24.6

Molecular peak in mass spectrum: m/e=586

Intense peaks: 427, 337, 247, 197, 129, 117.

Minor characteristic fragments: 452, 297, 223.

e. In the same way 9-keto-15α-hydroxy-prosta-5(c),8(12),13(t)-trienoic acid ($PGB_2$) was converted into 9-keto-15α, 18ξ-dihydroxy-prost-5(c),8(12), 13(t)-trienoic acid and 9-keto-15α,19ξ-dihydroxy-prosta-5(c),8(12),13(t)-trienoic acid. The protected 18-hydroxy compound (silyl ether, methyl ester, methoxime) has:

C-value: 27.2

Molecular peak in mass spectrum: m/e=537

Intense peaks: 506, 416, 360, 131.

Minor characteristic fragments: 418, 378, 326, 162.

The protected 19-hydroxy derivative has:

C-value: 27.7

Molecular peak in mass spectrum: m/e=537

Intense peaks: 506, 416, 129, 117.

Minor characteristic fragments: 378, 346, 326, 162.

f. In the same way 9-keto-15α-hydroxy-prosta-5(c),10,13(t)-trienoic acid ($PGA_2$) was converted into 9-keto-15α,18ξ-dihydroxy-prosta-5(c),13(t)-dienoic acid and 9-keto-15α, 19ξ-dihydroxy-prosta-5(c),13(t)-dienoic acid.

The protected 18-hydroxy compound has:

C-value: 25.9

Molecular peak in the mass spectrum: m/e=539

Intense peaks: 508, 418, 131, 129.

MInor characteristic fragments: 438, 380, 226, 220, 197.

The protected 19-hydroxy derivative has:

C-value: 26.2

Molecular peak in mass spectrum: m/e=539.

Intense peaks: 508, 418, 380, 348, 143, 129, 117.

Minor characteristic fragments: 438, 226, 220.

g. In the same way dl-9β,15α-dihydroxy-prost-13(t)-enoic acid, prepared according to Preparations 4 and 8, was converted into 9β, 15α,18ξ-trihydroxy-prost-13(t)-enoic acid and 9β, 15α, 19ξ-trihydroxy-prost-13(t)-enoic acid. The silylated methyl ester of the 18-hydroxy compound has:

C-value: 24.3

Molecular peak in mass spectrum: m/e=586

Intense peaks: 427, 337, 247, 197, 131, 129.

Minor characteristic fragments: 557, 467, 377, 350, 297, 223.

The silylated methyl ester of the 19-hydroxy compound has:

C-value: 124.6

Molecular peak in mass spectrum: m/e=586

Intense peaks: 427, 337, 247, 197, 129, 117.

Minor characteristic fragments: 452, 297, 223.

h. In the same way dl-9α,15α-dihydroxy-prost-13(t)-enoic acid, prepared according to Preparations 4 and 8, was converted into 9α, 15α, 18ξ-trihydroxy-prost-13(t)-enoic acid and 9α, 15α, 19ξ-trihydroxy-prost-13(t)-enoic acid.

The silylated methyl ester of the 18-hydroxy product has:

C-value: 24.2

Molecular peak in mass spectrum: m/e=586

Intense peaks: 427, 337, 297, 197, 131, 129.

Minor characteristic fragments: 557, 496, 467, 377, 350, 310, 247, 144.

The silylated methyl ester of the 19-hydroxy compound has:

C-value: 24.5

Molecular peak in mass spectrum: m/e=586

Intense peaks: 427, 337, 297, 197, 143, 129, 117.

Minor characteristic fragments: 496, 452, 310, 247, 143.

EXAMPLE II

An agar slant of Delacroixia coronata (CBS 647.68) was used to inoculate 100 ml of sterile 20—20 medium in a 500 ml conical flask. This medium as prepared as described in Example Ia.

The flask was incubated during 72 hours at 26° C. on a rotary shaker (280 r.p.m. 2.5 cm stroke). From the culture obtained 5 ml were used to inoculate 100 ml of sterile 10—10 medium in a 500 ml conical flask. The medium was prepared as described in Example Ia. The flask was incubated at 26° C. on the rotary shaker.

18 Hours after inoculation 2 mg of dl-9α, 15α-dihydroxy-15β-methyl-prost-13(t)-enoic acid, prepared according to Preparations 6 and 8, dissolved in 2.5 ml of 50% aqueous ethanol, were added and the incubation was continued for another 24 hours at 26° C. Hereafter the culture broth was filtered, the filtrate acidified to pH=3 with a 10% aqueous citric acid solution and extracted three times with 20 ml of ethyl acetate. The extract was evaporated in vacuo and the residue purified by column chromatography ($SiO_2$ pretreated with 1% acetic acid; eluted with ethyl acetate-heptanol (8.3) containing 0.1% acetic acid). The matching fractions were combined and evaporated in vacuo yielding 2.0 mg of 9α, 15α, 18ξ-trihydroxy-15β-methyl-prost-13(t)-enoic acid and 3.8 mg of 9α,15α, 19ξ-trihydroxy-15β-methyl-prost-13(t)-enoic acid.

The silylated methyl ester of the 18-hydroxy product has:

C-value: 24.2

Molecular peak in mass spectrum: m/e=600

Intense peaks: 441, 351, 297, 211, 42, 131.

Minor characteristic fragments: 585, 571, 481, 323, 301, 257, 144.

The protected 19-hydroxy product has:

C-value: 124.6
Molecular peak in mass spectrum: m/e=600
Intense peaks: 441, 351, 297, 143, 117.
Minor characteristic fragments: 585, 323, 301, 211.

b. In the same way dl-9-keto-15β-hydroxy-15α-methyl-20-ethyl-prost-13(t)-enoic acid, prepared according to Preparations 7 and 8, was converted into 9-keto-15β,18ξ-dihydroxy-15α-methyl-20-ethyl-prost-13(t)-enoic acid and 9-keto-15β,19ξ-dihydroxy-15α-methyl-20-ethyl-prost-13(t)-enoic acid.

The protected 18-hydroxy product (silyl ether, methoxime, methyl ester) has:
C-value: 27.0
Molecular peak in mass spectrum: m/e=583
Intense peaks: 396, 143.
Minor characteristic fragments: 526, 462, 436, 366, 364, 171, 159.

The protected 19-hydroxy product has:
C-value: 27.4
Molecular peak in mass spectrum: m/e=583
Intense peaks: 396, 171, 145, 143.
Minor characteristic fragments: 462, 450, 366, 364, 239.

EXAMPLE III a. An agar slant of Streptomyces sp. (CBS 188.74) was used to inoculate 100 ml of the following medium in a 500 ml conical flask: peptone 10 g/l, malt paste 15 g/l, NaCl 5 g/l, distilled water; the pH was adjusted to 7.2 with the aid of 30% aqueous potassium hydroxide solution. Sterilization was effected for 20 minutes at 120° C.

The flask was incubated during 72 hours at 26° C. on a rotary shaker (280 r.p.m., 2.5 cm stroke). From the culture obtained 5 ml were used to inoculate 100 ml of the following medium in a 500 ml conical flask: glucose 10 g/l, corn steep solids 3 g/l, peptone 5 g/l, NaCl 5 g/l, tap water; the pH was adjusted to 7.2 with the aid of a 30% aqueous potassium hydroxide solution. Sterilization was effected for 20 minutes at 120° C.

The flask was incubated for 72 hours at 26° C. on the rotary shaker. Hereafter 20 mg of 9-keto-11α,15α-dihydroxy-prost-13(t)-enoic acid ($PGE_1$), dissolved in 2.5 ml of 50% aqueous ethanol, were added and the incubation was continued for another 24 hours. According to thin layer chromatography two compounds were formed which were more polar than the starting material. The fermentation broth was filtered, the filtrate acidified to pH=3 with a 10% aqueous citric acid solution, and extracted three times with 30 ml of ethyl acetate. The extract was evaporated under reduced pressure and the residue purified by column chromatography ($SiO_2$ pretreated with 1% acetic acid and 19% water; eluted with ethyl acetate containing 0.1% acetic acid). The matching fractions were combined and evaporated under reduced pressure. The less polar of the two transformation products was obtained in 5.0 mg yield as an oil and proved to be 9-keto-11α,15α,18ξ-trihydroxy-prost-13(t)-enoic acid, according to combined GLC-mass spectrometry. The protected product has:
C-value: 26.6
Molecular peak in mass spectrum: m/e=629
Intense peaks: 297, 133, 131, 129.
Minor characteristic fragments: 598, 510, 470, 420, 380, 366, 310, 223, 197, 144.

The more polar of the transformation products was also obtained as an oil (yield 4 mg). This compound proved to be 9-keto-11α,15α,19ξ-trihydroxyprost-13(t)-enoic acid, according to combined GLC-mass spectrometry.

The protected compound has:
C-value: 27.0
Molecular peak in mass spectrum: m/e=629
Intense peak: 366, 297, 223, 183, 143, 133, 129, 117.
Minor characteristic fragments: 598, 470, 380, 197.

b. In the same way 9-keto-11α,15α-dihydroxy-prosta-5(c),13(t)-dienoic acid ($PGE_2$) was transformed into
9-keto-11α,15α,18ξ-trihydroxy-prosta-5(c),13(t)-dienoic acid and
9-keto-11α,15α,19ξ-trihydroxy-prosta-5(c),13(t)-dienoic acid.

The protected 18-hydroxy compound has:
C-value: 26.6
Molecular peak in mass spectrum: m/e=627
Intense peaks: 596, 506, 366, 295, 123, 133, 131, 129.
Minor characteristic fragments: 508, 468, 418, 378, 364, 197, 144.

The protected 19-hydroxy compound has:
C-value: 26.9
Molecular peak in mass spectrum: m/e=627
Intense peaks: 596, 506, 366, 295, 223, 143, 133, 129, 117.
Minor characteristic fragments: 468, 378, 364, 197.

c. In the same way 9α,11α,15α-trihydroxy-prosta-5(c),13(t)-dienoic acid ($PGF_{2\alpha}$) was transformed into 9α,11α,15α,18ξ-tetrahydroxy-prosta-5(c),13(t)-dienoic acid and 9α,11α,15α,19ξ-tetrahydroxy-prosta-5(c),13(t)-dienoic acid.

The protected 18-hydroxy product has:
C-value: 25.0
Molecular peak in mass spectrum: m/e=672
Intense peaks: 423, 333, 307, 217, 197, 191, 171, 131, 129.
Minor characteristic fragments: 643, 582, 553, 513, 481, 397.

The protected 19-hydroxy product has:
C-value: 25.3
Molecular peak in mass spectrum: m/e=672
Intense peaks: 423, 333, 307, 217, 197, 191, 143, 129, 117.
Minor characteristic fragments: 657, 582, 567, 531, 513, 481, 397.

d. In the same way dl-9α,15α,-dihydroxy-20-ethyl-prost-13(t)-enoic acid, prepared according to Preparations 4 and 8, was transformed into 9α,15α,18ξ-trihydroxy-20-ethyl-prost-13(t)-enoic acid and 9α,15α,19ξ-trihydroxy-20-ethyl-prost-13(t)-enoic acid.

The protected 18-hydroxy product has:
C-value: 25.6
Molecular peak in mass spectrum: m/e=614
Intense peaks: 427, 337, 297, 129.
Minor characteristic fragments: 557, 467, 377, 225, 159.

The protected 19-hydroxy compound has:
C-value: 25.9
Molecular peak in mass spectrum: m/e=614
Intense peaks: 427, 337, 297, 129.
Minor characteristic fragments: 571, 481, 391, 225, 145.

e. In the same way dl-9α,15α-dihydroxy-15β-methyl-20-ethyl-prost-13(t)-enoic acid, prepared according to Preparations 6 and 8, was transformed into 9α,15α,18ξ-trihydroxy-15β-methyl-20-ethyl-prost-13(t)-enoic acid and 9α,15α,19ξ-trihydroxy-15β-methyl-20-ethyl-prost-13(t)-enoic acid.

The protected product has:

C-value: 25.3
Molecular peak in mass spectrum: m/e=628
Intense peaks: 441, 351, 297, 159, 143.
Minor characteristic fragments: 571, 481, 323, 239.
The protected 19-hydroxy derivative has:
C-value: 25.9
Molecular peak in mass spectrum: m/e=628
Intense peaks: 441, 351, 297, 145, 143.
Minor characteristic fragments: 585, 495, 323, 239.

f. In the same way dl-9α,15β-dihydroxy-15α-methyl-20-ethyl-prost-13(t)-enoic acid, prepared according to Preparations 6 and 8, was transformed into 9α,15β,18ξ-trihydroxy-15α-methyl-20-ethyl-prost-13(t)-enoic acid and 9α,15β,19ξ-trihydroxy-15α-methyl-20-ethyl-prost-13(t)-enoic acid.

The protected 18-hydroxy compound has:
C-value: 25.3
Molecular peak in mass spectrum: m/e=628
Intense peaks: 441, 351, 297, 159, 143.
Minor characteristic fragments: 571, 481, 323, 239.
The protected 19-hydroxy product has:
C-value: 25.9
Molecular peak in mass spectrum: m/e=628
Intense peaks: 441, 351, 297, 145, 143.
Minor characteristic fragments: 585, 495, 323, 239.

The fermentations with other Streptomyces species were all carried out according to the procedure described in Example III; the fermentations with the other microorganisms were carried out according to the procedure described in Example I.

EXAMPLE IV a. Fermentation of dl-9β,15α-dihydroxy-prost-13(t)-enoic acid prepared according to Preparations 4 and 8, with Ophiobolus graminis (ATCC 12761) yielded a small amount of 9β,15α,17ξ-trihydroxy-prost-13(t)-enoic acid. The main products of these fermentations were the corresponding 18- and 19-hydroxy isomers, which were identical to the products of Example I g.

The silylated methyl ester of the 17-hydroxy compound has:
C-value: 23.7
Molecular peak in mass spectrum: m/e=586
Intense peaks: 427, 337, 223, 197, 145, 129.
Minor characteristic fragments: 543, 483, 453, 297, 259, 103.

b. In the same way dl-9-keto-15β-hydroxy-prost-13(t)-enoic acid, prepared according to the Preparations 3 and 8, when fermented with Streptomyces sp. (190.74) yielded a small amount of 9-keto-15β,17ξ-dihydroxy-prost-13(t)-enoic acid, next to the 18- and 19-hydroxy isomers, which were identical to the products of Example I b.

The protected 17-hydroxy product (silyl ether, methyl ester, methoxime) has:
C-value: 25.3
Molecular peak in mass spectrum: m/e=541
Intense peaks: 420, 382, 366, 250, 197, 145.
Minor characteristic fragments: 498, 438, 408, 259, 103.

c. In the same way dl-9α,15α-dihydroxy-prost-13(t)-enoic acid, prepared according to Preparations 4 and 8, when fermented with Streptomyces aureofaciens (ATCC 10762) yielded the 19-hydroxy derivative as the main product and small amounts of the 18-hydroxy derivative and 9α,15α,17ξ-trihydroxy-prost-13(t)-enoic acid as byproducts; the 18-hydroxy and 19-hydroxy derivatives were identical to the products of Example I c. The silylated methyl ester of the 17-hydroxy compound has:
C-value: 23.7
Molecular peak in mass spectrum: m/e=586
Intense peaks: 427, 337, 297, 197, 145
Minor characteristic fragments: 543, 483, 453, 247, 103.

d. In the same way dl-9β,15β-dihydroxy-prost-13(t)-enoic acid, prepared according to Preparations 4 and 8, when fermented with metarrhizium brunneum (CBS 316.51) yielded the 18- and 19-hydroxy derivatives as main products (which were identical to the products of Example I d) and 9β,15β,17ξ-trihydroxy-prost-13(t)-enoic acid as byproduct.

The silylated methyl ester of the 17-hydroxy compound has:
C-value: 23.7
Molecular peak in mass spectrum: m/e=586
Intense peaks: 427, 337, 223, 197, 145, 129.
Minor characteristic fragments: 543, 483, 453, 297, 259, 103.

e. In the same way dl-9α,15β-dihydroxy-prost-13(t)-enoic acid, prepared according to Preparations 4 and 8, when fermented with Streptomyces griseus (CBS 479.48) yielded a small amount of 9α,15β,17ξ-trihydroxy-prost-13(t)-enoic acid, next to the 18- and 19-hydroxy isomers, which were identical to the products of Example I h.

The silylated methyl ester of the 17-hydroxy compound has:
C-value: 23.7
Molecular peak in mass spectrum: m/e=586
Intense peaks: 427, 337, 297, 197, 145.
Minor characteristic fragments: 543, 483, 453, 247, 103.

EXAMPLE V a. A culture of Stemphylium solani (NRRL 1805) was grown in a 10—10 medium according to the procedure described in Example I a.

18 Hours after inoculation 20 mg of dl-9α,15β-dihydroxy-prost-13(t)-enoic acid, prepared according to Preparations 4 and 8, dissolved in 2.5 ml of 50% aqueous ethanol were added and the incubation was continued for another 24 hours at 26° C.

According to TLC a new compound was formed which was more polar than the starting material. The fermentation broth as filtered, the filtrate acidified to pH=3 with a 10% aqueous citric acid solution, and extracted three times with 20 ml of ethyl acetate. The extract was evaporated under reduced pressure and the residue purified by column chromatography ($SiO_2$ pretreated with 1% acetic acid; eluted with ethyl acetate-heptane (8:3) containing 0.1% acetic acid). The matching fractions were combined and evaporated under reduced pressure.

There was obtained 7 mg of 9α,15β,20-trihydroxy-prost-13(t)-enoic acid. The silylated methyl ester of this product has:
C-valve: 25.5
Molecular peak in mass spectrum: m/e=586
Intense peaks: 427, 337, 297, 129.
Minor characteristic fragments: 367, 197, 170, 142, 103.

b. In the same way dl-9β,15β-dihydroxy-prost-13(t)-enoic acid, prepared according to Preparations 4 and 8, was converted into 9β,15β,20-trihydroxyprost-13(t)-enoic acid.

The silylated methyl ester of this product has:
C-valve: 25.5
Molecular peak in mass spectrum: m/e=586
Intense peaks: 427, 337, 129.
Minor characteristic fragments: 367, 297, 197, 170, 142, 103.

c. In the same way 9-keto-15α-hydroxy-prosta-5(c),8(12),13(t)-trienoic acid ($PGB_2$) was converted by Aspergillus niger (ATCC 9142) into 9-keto-15α,20-dihydroxyprosta-5(c),8(12),13(t)-trienoic acid.
The protected product has:
C-valve: 28.5
Molecular peak in mass spectrum: m/e=537
Intense peaks: 506, 416, 378, 162.
Minor characteristic fragments: 436, 246, 232, 184, 103.

d. In the same way 9-keto-15α-hydroxy-prosta-5(c),10,13(t)-trienoic acid ($PGA_2$) was transformed by Preussia fleischhakii (CBS 167.40) into 9-keto-15α,20,-dihydroxy-prosta-5(c),13(t)-dienoic acid.
The protected product has:
C-value: 27.1
Molecular peak in mass spectrum: m/e=539
Intense peaks: 508, 129.
Minor characteristic fragments: 438, 380, 348, 226, 220, 198, 184, 142, 103.

e. In the same way dl-9-keto-15α-hydroxy-15β-methyl-20-ethyl-prost-13(t)-enoic acid, prepared according to Preparations 7 and 8, was convertd by Preussia fleischhakii (CBS 167.40) into 9-keto-15α,20ξ-dihydroxy-15β-methyl-20 -ethyl prost-13(t)-enoic acid.
The protected product has:
C-valve: 27.8
Molecular peak in mass spectrum: m/e=583
Intense peaks: 396, 143, 131.
Minor characteristic fragments: 464, 462, 366, 364, 239, 144.

f. In the same way dl-9-keto-15β-hydroxy-15α-methyl-20-ethyl-prost-13(t) enoic acid, prepared according to Preparations 7 and 8, was transformed by Preussia fleischhakii (CBS 167.40) into 9-keto-15β,20ξ-dihydroxy-15α-methyl-20 -ethyl-prost-13(t)-enoic acid.
The protected product has:
C-value: 27.8
Molecular peak in mass spectrum: m/e=583
Intense peaks: 396, 142, 131.
Minor characteristic fragments: 464, 462, 366, 239.

g. In the same way dl-9α,15α-dihydroxy-20 ethyl-prost-13(t)-enoic acid, prepared according to Preparations 4 and 8, was converted into 9α,15α,20ξ-trihydroxy-20ξ-ethyl-prost-13(t)-enoic acid.
The protected product has:
C-value: 26.3
Molecular peak in mass spectrum: m/e=614
Intense peaks: 427, 337, 297, 246, 131, 129.
Minor characteristic fragments: 585, 495, 323, 310, 211.

h. In the same way dl-9α,15α-dihydroxy-15β-methyl-20-ethyl-prost-13(t)-enoic acid, prepared according to Preparations 6 and 8, was transformed into 9α,15α,20ξ-trihydroxy-15β-methyl-20ξ-ethyl-prost-13(t)-enoic acid.
The protected product has:
C-value: 26.2
Molecular peak in mass spectrum: m/e=628
Intense peaks: 441, 351, 297, 143, 131.
Minor characteristic fragments: 509, 419, 323, 239.

i. In the same way dl-9α,15β-dihydroxy-15α-methyl-20-ethyl-prost-13(t)-enoic acid, prepared according to Preparations 6 to 8, was converted into 9α,15β,20 -trihydroxy-15α-methyl-20ξ-ethyl-prost-13(t)-enoic acid.
The protected product has:
C-value: 26.3
Molecular peak in mass spectrum: m/e=628
Intense peaks: 441, 351, 297, 143, 131.
Minor characteristic fragments: 509, 419, 323, 239.

j. In the same way dl-9-keto-15α-hydroxy-prost-13(t)-enoic acid, prepared according to Preparations 3 and 8, was converted by Pythium ultimum (CBS 296.37) into 9-keto-15α20-dihydroxy-prost-13(t)-enoic acid.
The protected product has:
C-value: 27.2
Molecular peak in mass spectrum: m/e=541
Intense peaks: 510, 382, 222, 129.
Minor characteristic fragments: 420, 368, 309, 197, 103.

k. In the same way dl-9-keto-15β-hydroxy-prost-13(t)-enoic acid, prepared according to Preparations 3 and 8, was converted by Curvularia trifolli (CBS 210.59) into 9-keto-15β,20-dihydroxy-prost-13(t)-enoic acid.
The protected product has:
C-value: 27.4
Molecular peak in mass spectrum: m/e=541
Intense peaks: 510, 382, 222, 129.
Minor characteristic fragments: 420, 368, 309, 197, 103.

l. In the same way dl-9β,15α-dihydroxy-prost-13(t)-enoic acid, prepared according to Preparations 4 and 8, was converted by Alternaria radicina (CBS 245.67) into 9β,15α,*-trihydroxy-prost-13(t)-enoic acid.
The protected product has:
C-value: 25.5
Molecular peak in mass spectrum: m/e=586
Intense peaks: 427, 337, 129.
Minor characteristic fragments: 313, 297, 197, 142, 103.

When the mold Delacroixia coronata (CBS 476.68) was fermented with the substrates mentioned in Examples V h and v i, the same 20-hydroxy derivatives were obtained, but as byproduct only. Main products with this microorganism were then the 19-hydroxy derivatives of these substrates.

EXAMPLE VI a. 10 mg of 9-keto-11α,15α,18ξ-trihydroxy-prost-13(t)-enoic acid, prepared according to Example III a, were dissolved in 1 ml of methanol. To this solution 4 ml of an ethereal solution of diazomethane (containing tes the reaction was completed. The solvent was evaporated in a stream of nitrogen and methyl 9-keto-11α,1-5α,18ξ-trihydroxy-prost-13(t)-enoate was obtained as an oil.

b. 3.7 mg of 9-keto-11α,15α,19 -trihydroxy-prost-13(t)-enoic acid, prepared according to Example III a, were dissolved in 0.5 ml of ethyl acetate. To the solution was added a solution of 1.5 mg of triethanolamine in 0.5 ml of ethyl acetate. The resulting solution was evaporated to dryness in a stream of nitrogen and then dried in vacuum to constant weight; 9-keto-11α,1-5α,19ξ-trihydroxy-prost-13(t)-enoic acid triethanolamine salt obtained as an oil.

Other microorganisms capable of introducing an 18-, 19- or 20-hydroxy group in the prostaglandin compounds of formula II are, for example:
Aspergillus amstelodami (CBS 521.65)

Aspergillus chevalieri (CBS 414.67)
Aspergillus flavus (CBS 178.74)
Beauveria alba (CBS 348.55)
Botryosphaeria rhodina (CBS 175.26)
Botrytis cinerea (ATCC 12481)
Coprinus bisporus (CBS 184.52)
Corpinus congregatus (CBS 180.51)
Cunninghamella blakesleeana (NRRL 1373)
Cunninghamella echinulata (CBS 229.51)
Curvularia ellisii (CBS 193.62)
Diplodia alni (CBS 200.49)
Drechslera buchloes (CBS 246.49)
Endothiella gyrosa Sacc. (CBS 253.54)
Entomophtora virulenta (CBS 217.66)
Fusarium semitectum (CBS 181.74)
Fusarium ventricosum (CBS 205.31)
Gliocladium viride Matr. (CBS 191.32)
Gongronella butleri (CBS 259.52)
Hormodendrum chaquense (CBS 231.36)
Hypomyces aurantius (CBS 207.29)
Hypoxylon haematostroma (CBS 255.63)
Hypoxylon jecorinum (CBS 258.63)
Isoachlya turoloides (CBS 598.67)
Lycoperdon gemmatum (CBS 182.74)
Microascus cinereus (CBS 300.61)
Microascus cirrosus (CBS 277.24)
Microascus desmospours (CBS 424.62)
Mycoacia stenodon (CBS 318.54)
Nigrospora sacchari (CBS 290.62)
Nodulisporium verrucosum (CBS 245.29)
Paecilomyces cremeo-roseus (CBS 250.55)
Paecilomyces farinosus (CBS 183.74)
Pellicularia filamentosa (CBS 184.74)
Pestalotia populi-nigrae (CBS 353.51)
Petriella asymmetrica (CBS 297.58)
Petriellidium boydii (CBS 593.73)
Petriellidium ellipsoideum (CBS 418.73)
Physalospora mutila (CBS 302.36)
Physalospora rhodina (CBS 185.74)
Pseudonectria pachysandricola (CBS 501.63)
Rhizopus nigricans (ATCC 6227$^b$)
Sepedonium chrysospermum (CBS 140.23)
Septoria linicola (CBS 502.50)
Sphaeropsis conspersa (CBS 209.25)
Stemphylium consortiale (NRRL 2187)
Thielavia basicola (CBS 540.50)
Thielavia terricola (CBS 165.73)
Verticillium lecanii (CBS 123.42)

Moreover, an 18- or 19-hydroxy group can also be introduced in the prostaglandin compounds of formula II by various species of the genus Streptomyces, for example the species:

Streptomyces chattanoogenis (ATCC 19673)
Streptomyces chattanoogensis (ATCC 13358)
Streptomyces natalensis (CBS 700.57)

and the species with the following CBS deposit numbers:

186.74, 187.74, 189.74, 190.74, 191.74, 192.74, 193.74, 193.74 and 194.74.

We claim:

[1. The 18 - and 19 - hydroxy-prostaglandins, of the formula:]

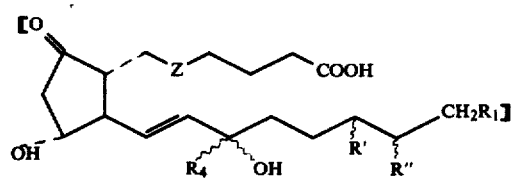

[wherein the waved lines indicate that the substituents at the representative bonds are either in the $\alpha$ or $\beta$ position; Z represents —$CH_2CH_2$— or cis —CH=CH—; $R_1$ represents H, $CH_3$— or $C_2H_5$—; $R_4$ is hydrogen or methyl and one of R' and R'' is hydroxy and the other is hydrogen and pharmaceutically acceptable salts or the aliphatic esters thereof containing 1 to 5 carbon atoms.]

[2. A compound according to claim 1, which is 9-keto-11$\alpha$,15$\alpha$,18$\xi$-trihydroxy-prost-13(t)-enoic acid.]

3. A compound [according to claim 1] which is 9-keto-11$\alpha$,15$\alpha$,19$\xi$-trihydroxy-prost-13(t)-enoic acid.

[4. A compound according to claim 1, which is 9-keto-11$\alpha$,15$\alpha$,18$\xi$-trihydroxy-prosta-5(c),13(t)-dienoic acid.]

[5. A compound according to claim 1, which is 9-keto-11$\alpha$,15$\alpha$,19$\xi$-trihydroxy-prosta-5(c),13(t)-dienoic acid.]

[6. A compound according to claim 1, which is methyl 9-keto-11$\alpha$,15$\alpha$,18$\xi$-trihydroxy-prost-13(t)-enoate.]

[7. A compound according to claim 1, which is 9-keto-11$\alpha$,15$\alpha$,19$\xi$-trihydroxy-prost-13(t)-enoic acid triethanolamine salt.]

*8. A compound which is selected from 9-keto-11$\alpha$, 15$\alpha$,19$\xi$-trihydroxy-prost-13(t)-enoic acid, pharmaceutically acceptable salts or aliphatic esters thereof containing 1 to 5 carbon atoms.*

* * * * *